(12) United States Patent
Ordidge

(10) Patent No.: US 10,564,240 B2
(45) Date of Patent: Feb. 18, 2020

(54) METHOD AND SYSTEM FOR MAGNETIC RESONANCE IMAGING USING SLICE SELECTIVE PULSES

(71) Applicant: The University of Melbourne, Victoria (AU)

(72) Inventor: Roger John Ordidge, Victoria (AU)

(73) Assignee: The University of Melbourne, Victoria (AU)

(*) Notice: Subject to any disclaimer, the term of this patent is extended or adjusted under 35 U.S.C. 154(b) by 0 days.

(21) Appl. No.: 15/548,734

(22) PCT Filed: Feb. 5, 2016

(86) PCT No.: PCT/AU2016/050068
§ 371 (c)(1),
(2) Date: Aug. 3, 2017

(87) PCT Pub. No.: WO2016/123674
PCT Pub. Date: Aug. 11, 2016

(65) Prior Publication Data
US 2018/0031656 A1 Feb. 1, 2018

(30) Foreign Application Priority Data

Feb. 6, 2015 (AU) .................................. 2015900378
Jan. 19, 2016 (AU) .................................. 2016900158

(51) Int. Cl.
*G01R 33/483* (2006.01)
*G01R 33/565* (2006.01)
*G01R 33/24* (2006.01)
*G01N 24/12* (2006.01)
(Continued)

(52) U.S. Cl.
CPC ......... *G01R 33/4833* (2013.01); *G01R 33/24* (2013.01); *G01R 33/5659* (2013.01); *G01N 24/12* (2013.01); *G01Q 60/52* (2013.01); *G01R 33/32* (2013.01)

(58) Field of Classification Search
CPC ................ G01R 33/4833; G01R 33/24; G01R 33/5659; G01R 33/32
See application file for complete search history.

(56) References Cited

U.S. PATENT DOCUMENTS

| 4,699,148 A | 10/1987 | Gyngell |
| 5,049,820 A * | 9/1991 | Briand ............... G01R 33/4833 324/309 |
| 5,125,407 A * | 6/1992 | Harms ................. G01R 33/561 324/309 |

(Continued)

OTHER PUBLICATIONS

Bernstein et al., "Handbook of MRI Pulse Sequences", Elsevier: Academic Press, pp. 67-76.

(Continued)

*Primary Examiner* — G. M. A Hyder
(74) *Attorney, Agent, or Firm* — Knobbe Martens Olson & Bear LLP

(57) ABSTRACT

An MRI pulse sequence is disclosed. The pulse sequence involves a plurality of slice selective pulses (51,55) which each individually have a desired rotation that is less than or equal to the total desired rotation. The slice selective pulses each cause a rotation about respective axes, which may be different to each other. Optionally phase correction (rephasing) gradients (53, 56) can also be included in the pulse sequence.

19 Claims, 22 Drawing Sheets

(51) Int. Cl.
 *G01Q 60/52* (2010.01)
 *G01R 33/32* (2006.01)

(56) References Cited

U.S. PATENT DOCUMENTS

| | | | | |
|---|---|---|---|---|
| 5,218,531 | A | * | 6/1993 | Sekihara ............... G01R 33/56 324/309 |
| 5,345,178 | A | * | 9/1994 | Manabe ............... G01R 33/385 324/319 |
| 5,677,628 | A | * | 10/1997 | Watanabe .......... G01R 33/4833 324/307 |
| 6,005,391 | A | * | 12/1999 | Bornert ............... G01R 33/446 324/307 |
| 6,064,203 | A | | 5/2000 | Bottomley |
| 2007/0007959 | A1 | | 1/2007 | Szyperski et al. |
| 2011/0050227 | A1 | * | 3/2011 | Barrett ............... G01R 33/4641 324/310 |
| 2013/0057280 | A1 | | 3/2013 | Feiweier |

OTHER PUBLICATIONS

International Search Report and Written Opinion for International Application No. PCT/AU2016/050068 dated May 11, 2016 in 10 pages.

Ozturk et al., "Estimating Motion from MRI data", Proc IEEE Inst Electr Electron Eng., 2003 (Oct. 2003), vol. 91, No. 10, pp. 1627-1648. DOI: 10.1109/JPROC.2003.817872.

Haacke et al., "A Closer Look at Radiofrequency Pulses", Magnetic Resonance Imaging: Physical Principles and Sequence Design, Second Edition, Chapter 16, Apr. 22, 2014.pp. 388-392.

Hsu et al., "Mitigate B1+ inhomogeneity by slice-selective composite excitation pulses", Proc. Intl. Soc. Mag. Reson. Med. 21 (2013), p. 4247.

Thesen et al., "Compensation of dielectric resonance effects by means of composite excitation pulses", Proc. Intl. Soc. Mag. Reson. Med 11 (2003) p. 715.

* cited by examiner

METHOD AND SYSTEM FOR MAGNETIC RESONANCE IMAGING USING SLICE SELECTIVE PULSES

FIELD OF THE INVENTION

This invention generally relates to Magnetic Resonance Imaging. More specifically, the invention relates to radio-frequency magnetic field pulse sequences and associated magnetic field gradients.

BACKGROUND OF THE INVENTION

Magnetic Resonance Imaging (MRI) exploits the nuclear magnetic resonance (NMR) phenomena by combining NMR with gradient magnetic fields to allow cross-sectional slice-selective excitation of nuclei within a subject under examination. Typically, a pulse-sequence of radio-frequency magnetic fields (RF pulse) and associated magnetic field gradients is used with further two dimensional (2D) encoding of the NMR signals to create a 2D image of a portion of the subject. A 3D image of the subject can then be obtained by combining many slices together.

By increasing the static magnetic field strength (B0) an improved signal-to-noise ratio may be obtained along with improved spatial resolution in the images created. Ideally, in an MR system the RF pulse should deliver a defined rotation of the nuclear magnetization vector ($\alpha°$) to provide uniform signal strength over the dimensions of the sample. However, local magnetic and electrical field effects in the subject can lead to spatial inhomogeneity in the local radio-frequency (RF) transverse magnetic field (B1) the nuclei are exposed to. This affects imaging as the MRI pulse sequence employed may not result in the intended rotation of the nuclear magnetisation vector (M). Inhomogeneity in the B1 field is more problematic at B0 fields above 3 T and can lead to imaging artefacts which, in the worst case, are manifested as zero signal in some regions of the image. B1 inhomogeneity effects may also occur at low or medium B0 fields, and when inhomogeneous RF coils such as surface coils are used.

These problems can be addressed by using a multiplicity of transmit coils and activating them in a particular manner to attempt to generate a uniform B1 field. However the manner of activation cannot be pre-computed and must be calculated in real time while the subject is positioned in the imaging device and stationary. Moreover the calculations can take many minutes to complete, and while they are occurring the patient cannot move.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In order to address the drawbacks noted above, the present inventors have developed methods that can be implemented without the need for extensive real-time calculations. Most preferably they can be implemented in MRI systems using a single transmit coil.

Preferred embodiments use a MRI pulse sequence that aim, in total, to cause a desired total rotation of the net magnetisation vector representing a resultant magnetisation of the nuclear magnetic moments of an ensemble of nuclei in the portion of the subject. The pulse sequence involves a plurality of slice selective pulses which each individually have a desired rotation that is less than or equal to the total desired rotation. The slice selective pulses each cause a rotation about respective axes, which may be different to each other. In some embodiments, successive rotations are performed about alternating axes. In some forms the axes are orthogonal to each other. Optionally phase correction (re-phasing) gradients can also be included in the pulse sequence.

In a first aspect of the present invention, there is provided a method for use in magnetic resonance imaging including: exposing at least a portion of a subject to a longitudinal magnetic field (B0) such that a net magnetisation vector representing a resultant magnetisation of the nuclear magnetic moments of an ensemble of nuclei in the portion of the subject, is longitudinally aligned with the magnetic field (B0); performing a first slice-selective rotation by exposing at least said portion of the subject to a first radio-frequency magnetic field pulse (B1a) and a corresponding first magnetic field gradient to excite nuclei within the portion subject, the first radio-frequency magnetic field pulse being configured to rotate the net magnetisation about a first axis by a first angle such that a first component of the net magnetisation lies in a first plane including the first axis and a second component of the net magnetisation remains aligned with the magnetic field (B0); performing a second slice-selective rotation by exposing at least said portion of the subject to a second radio-frequency magnetic field pulse (B1b) and corresponding second magnetic field gradient to excite nuclei within the portion of the subject, the second radio-frequency magnetic field pulse being configured to rotate the net magnetisation about a second axis by a second angle such that at least a portion of the net magnetisation that remained aligned with the magnetic field (B0) after the first slice selective rotation lies in a plane including the second axis of rotation; and performing a final phase adjustment by exposing at least said portion of the subject to a final re-phasing magnetic field gradient to correct de-phasing of the magnetisation vectors within the ensemble that exist after the second slice-selective rotation.

In some cases additional slice selective rotations can be performed. In some embodiments a third slice-selective rotation can be performed by exposing at least said portion of the subject to a third radio-frequency magnetic field pulse (B1c) and a corresponding third magnetic field gradient to excite nuclei within the portion of the subject, the third radio-frequency magnetic field pulse being configured to rotate the net magnetisation about the first axis by a third angle; and the final phase adjustment is performed after the third slice selective rotation.

In a second aspect of the present invention, there is provided a method for use in magnetic resonance imaging including: exposing at least a portion of the subject to a longitudinal magnetic field (B0) such that a net magnetisation vector representing a resultant magnetisation of the nuclear magnetic moments of an ensemble of nuclei in the portion of the subject, is longitudinally aligned with the magnetic field (B0); performing a first slice-selective rotation by exposing at least said portion of the subject to a first radio-frequency magnetic field pulse (B1a) and a corresponding first magnetic field gradient to excite nuclei within the portion subject, the first radio-frequency magnetic field pulse being configured to rotate the net magnetisation about a first axis by a first angle such that a first component of the net magnetisation lies in a first plane including the first axis and a second component of the net magnetisation remains aligned with the magnetic field (B0); performing a first phase adjustment by exposing at least said portion of the subject to a first re-phasing magnetic field gradient to correct de-phasing of magnetisation vectors within the ensemble that is a result of the first slice-selective rotation, and to over-correct said de-phasing of the magnetisation vectors within the ensemble; performing a second slice-selective rotation by exposing at least said portion of the subject to a second radio-frequency magnetic field pulse (B1b) and corresponding second magnetic field gradient to excite nuclei within the portion of the subject, the second radio-frequency magnetic field pulse being configured to rotate the net magnetisation about a second axis by a second angle such that at least a portion of the net magnetisation that remained aligned with the magnetic field (B0) after the first slice selective rotation lies in a plane including the second axis of rotation; and performing a final phase adjustment by exposing at least said portion of the subject to a final re-phasing magnetic field gradient to correct de-phasing of the magnetisation vectors within the ensemble that is a result of the second slice-selective rotation.

In some cases additional slice selective rotations can be performed. In some embodiments a third slice-selective rotation can be performed by exposing at least said portion of the subject to a third radio-frequency magnetic field pulse (B1c) and a corresponding third magnetic field gradient to excite nuclei within the portion of the subject, the third radio-frequency magnetic field pulse being configured to rotate the net magnetisation about the first axis by a third angle.

In a third aspect of the present invention, there is provided a method for use in magnetic resonance imaging including exposing at least a portion of the subject to a longitudinal magnetic field (B0) such that a net magnetisation vector representing a resultant magnetisation of the nuclear magnetic moments of an ensemble of nuclei in the portion of the subject, is longitudinally aligned with the magnetic field (B0); performing a first slice-selective rotation by exposing at least said portion of the subject to a first radio-frequency magnetic field pulse (B1a) and a corresponding first magnetic field gradient to excite nuclei within the portion of the subject, the first radio-frequency magnetic field pulse being configured to rotate the net magnetisation about a first axis by a first angle such that a first component of the net magnetisation lies in a first plane including the first axis and a second component of the net magnetisation remains aligned with the magnetic field (B0), and wherein within the portion of the subject the first magnetic field gradient results in a magnetic field with a magnitude that increases along a first gradient direction; performing a second slice-selective rotation by exposing at least said portion of the subject to a second radio-frequency magnetic field pulse (B1b) and corresponding second magnetic field gradient to excite nuclei within the portion of the subject, the second radio-frequency magnetic field pulse being configured to rotate the net magnetisation about a second axis by a second angle such that at least a portion of the net magnetisation that remained aligned with the magnetic field (B0) after the first slice selective rotation lies in a plane including the second axis of rotation, and wherein the second magnetic field gradient results in a magnetic field with a magnitude that decreases along the first gradient direction and at least partly re-phases a de-phasing of the magnetisation vectors within the ensemble that is a result of the first slice-selective rotation.

In some forms the present invention provides a method in an MRI system and magnetic resonance imaging pulse that includes three components. Most preferably the first and third components induce a rotation in the same direction, while the second induces a rotation in a different (preferably orthogonal direction).

The pulse sequence has a desired net rotation, but the summed desired rotation of its components are greater than the desired net rotation. For example in a case where a desired net rotation is 180 degrees the components can be 90 degree rotations, and the summed desired rotations of its components are 270 degrees.

In a fourth aspect of the invention there is provided a method for use in magnetic resonance imaging including exposing at least a portion of a subject to a longitudinal magnetic field (B0) such that a net magnetisation vector representing a resultant magnetisation of the nuclear magnetic moments of an ensemble of nuclei in the portion of the subject, is longitudinally aligned with the magnetic field (B0); performing a first slice-selective rotation by: exposing at least said portion of the subject to a first radio-frequency magnetic field pulse (B1a) and a corresponding first magnetic field gradient to excite nuclei within the portion subject, the first radio-frequency magnetic field pulse being configured to rotate the net magnetisation about a first axis by a first angle such that a first component of the net magnetisation lies in a first plane including the first axis and a second component of the net magnetisation remains aligned with the magnetic field (B0); performing a second slice-selective rotation by: exposing at least said portion of the subject to a second radio-frequency magnetic field pulse (B1b) and corresponding second magnetic field gradient to excite nuclei within the portion of the subject, the second radio-frequency magnetic field pulse being configured to rotate the net magnetisation about a second axis by a second angle such that at least a portion of the net magnetisation that remained aligned with the magnetic field (B0) after the first slice selective rotation lies in a plane including the second axis of rotation; and performing a third slice-selective rotation by: exposing at least said portion of the subject to a third radio-frequency magnetic field pulse (B1c) and a corresponding third magnetic field gradient to excite nuclei within the portion of the subject, the third radio-frequency magnetic field pulse being configured to rotate the net magnetisation about the first axis by a third angle.

In a fifth aspect of the present invention, there is provided a magnetic resonance imaging (MRI) system including: magnetic field producing means for producing a magnetic field (B0); magnetic field gradient producing means configured to produce magnetic field gradients to alter the magnetic field B0 and produce an effective magnetic field; radio-frequency magnetic field generating means configured to produce radio-frequency magnetic fields (B1a and B1b); and positioning means for positioning at least part of a subject to be exposed to the effective magnetic field; wherein the system is configured to perform any one of the methods disclosed herein.

In other aspects of the present invention, there are provided magnetic resonance imaging (MRI) pulse sequences to be used with a magnetic resonance imaging system. The pulse sequences may be used by any one of the methods disclosed herein.

As noted above inhomogeneity in the B1 field is more problematic at B0 fields above 3 T, however application of the various aspects and embodiments of the present invention should not be considered to be limited to this field strength. Aspects and embodiments can find application at lower B0 levels, e.g. 1.5 T and above or perhaps lower. This is particularly the case for aspects or embodiments which increase the level of useable signal obtained from the MRI system.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
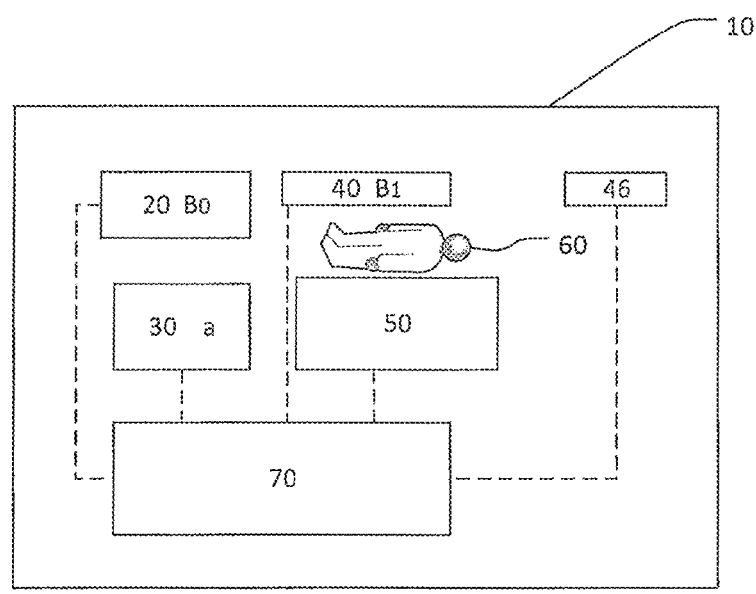
FIG. 1 is a block diagram of a magnetic resonance imaging system.

FIG. 1 shows a highly schematic block diagram for a Magnetic Resonance Imaging (MRI) system 10 including:
a magnetic field producing means 20;
a magnetic field gradient producing means 30;
a radio-frequency magnetic field generating means 40;
an RF receiver 46;
a positioning means 50; and
a control unit 70.

Figure 2A:
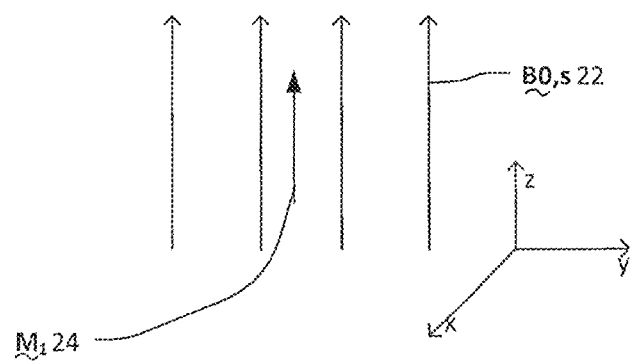
FIG. 2a is a vector diagram showing the equilibrium net magnetisation from an ensemble of nuclei in a uniform magnetic field B0.

The magnetic field producing means 20 is configured to produce a static uniform magnetic field B0,s, 22 aligned to a longitudinal direction along the z-axis (FIG. 2a). A preferred example of the field producing means 20 is a superconducting magnet system.

The magnetic field gradient producing means 30 is configured to produce a magnetic field gradient G, 32. This can be thought of an additional magnetic field that alters the magnetic field B0,s to produce a modified magnetic field B0, 24. The gradient is not strong enough to vary the direction of the field, so B0 is always parallel with B0,s in the longitudinal axis. Therefore it suffices to define B0 in terms of the component in the longitudinal direction and it is unnecessary to refer to it as a vector quantity. It will therefore be referred to as a scalar quantity B0 without loss of generality. As will be discussed further below, the gradient is used for slice selection.

The radio-frequency (RF) magnetic field generating means 40 is configured to produce transversely oriented RF magnetic fields B1a and B1b, i.e. oriented such that they lie in the x-y plane, that oscillate at a radio-frequency corresponding to the Larmor frequency of a nuclei of interest for MRI (typically protons or carbon-13) exposed to the magnetic field B0. The RF magnetic fields may be linearly or circularly polarised depending on the type of RF magnetic field generating means 40 used and have a phase defined by the operator.

The positioning means 50 is for positioning at least part of a subject 60 in the magnetic field B0.

The system also includes a RF receiver 46, such as RF receiver coils, for receiving an MRI signal. In some embodiments, the RF receiver is part of the RF magnetic field generating means 40. The RF receiver is typically only sensitive to RF magnetic fields oriented in the transverse plane.

In some embodiments, the system 10 includes a control unit 70. Control unit 70 is communicatively coupled with the other components (20, 30, 40, 50) of the system 10. Control unit 70 may include a storage means 72 for storing instructions that determine how the control unit 70 controls the other components (20, 30, 40, 50). Instructions include programs for generating MRI pulse sequences that vary the RF magnetic fields B1 and the magnetic field gradient G to selectively excite nuclei in a cross-sectional slice of the subject exposed to the magnetic field B0. By varying the gradients over two dimensions in k-space, the MRI signals can be spatially encoded to produce a 2D raw image (phase encoding, frequency encoding). Using known Fourier transform MRI techniques, the 2D raw image can be converted or transformed into a 2D image of a cross-sectional slice of the subject. Careful selection of pulse sequence parameters can be used to improve image contrast between various compounds or materials within the subject. By taking many 2D images a 3D image of the subject can be obtained.

The magnetic field producing means 20 may either be controlled by the control unit 70 or it may be persistently producing field B0 (as is usually the case for a superconducting magnet system). The magnetic field producing means 20 and magnetic field gradient producing means 30 may also be in communication with the control unit 70 such that the control unit can monitor their status and/or functionality. For example, the control unit 70 may monitor whether the correct magnetic field strength is being produced, either directly through measuring the proton frequency of the signal from water or indirectly by monitoring an electrical characteristic of the field producing means 20 such as power output.

The subject 60 contains an ensemble of nuclei each with a magnetic moment. When at least a portion of the subject 60 (therefore the ensemble of nuclei within the portion) is exposed to the magnetic field B0 it is considered that, statistically, a greater proportion of the nuclei's magnetic moments become aligned with the magnetic field B0. The time-averaged magnetisation of the portion exposed to the magnetic field B0 is, at equilibrium, described by a net magnetisation vector M, 24 parallel to the direction of the magnetic field B0 (FIG. 2a). At the start of an MRI pulse sequence, the magnetisation M is considered to be at equilibrium and oriented as shown in FIG. 2a.

As will be appreciated by the person skilled in the art, exposure of a subject to a magnetic field is not intended to be limited to mean exposure of a surface of the subject, or the near sub-surface, and is intended to include exposing the nuclei within and throughout the subject to said magnetic field. The use of the term is also intended to include the situation where the MRI system has a persistent magnetic field B0 and the subject is introduced into the field.

Rotation of Magnetisation Vector by RF Magnetic Fields

As is known in the art, a transverse RF magnetic field (B1) that is orthogonal to the main magnetic field B0 is typically used to cause rotation of the net magnetisation M, 24 away from the longitudinal axis (z-axis) so that a component of magnetization is created in the transverse plane. This is necessary for the RF receivers to measure a MRI signal. Typically, a 90° rotation is desired to completely rotate or flip the magnetisation into the transverse plane to maximise the MRI signal.

Figure 2B:
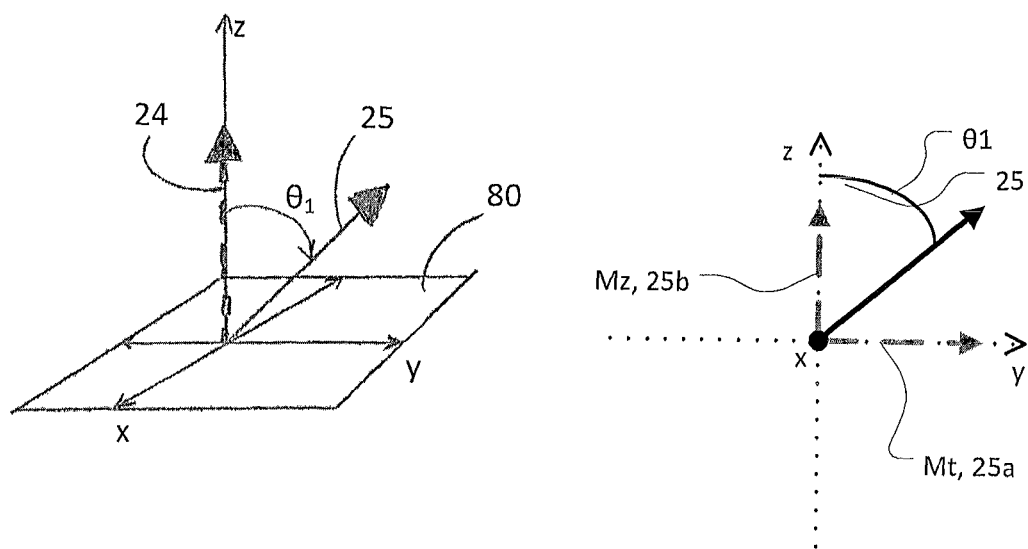
FIG. 2b illustrates a pair of vector diagrams, the leftmost being a three dimensional diagram, and the rightmost being a projection onto the y-z plane, each a first rotation of the net magnetisation when the ensemble of nuclei are excited by a suitable RF magnetic field.

As illustrated in FIGS. 2b and 2b, in an embodiment of the invention, an MRI sequence with two RF oscillating magnetic fields (B1a and B1b) is used to rotate the magnetisation vector M from its initial alignment in the z-direction towards (or close to) a transverse plane 80 (the x-y plane that is orthogonal to the z-axis).

FIG. 2b shows in its leftmost figure a three dimensional representation of a magnetisation M, and in its rightmost figure a projection of this rotation onto the y-z plane, to aid visualisation. In this example, the first RF magnetic field (B1a) excites the nuclei and causes a first rotation of the magnetisation M about a first axis (which is defined as the x-axis) by a first angle ($\theta 1$) towards the y-axis and therefore towards the transverse plane 80. As the magnetisation M is rotated away from its original equilibrium orientation 24 aligned with the z-axis, the rotated magnetization 25 can be considered to consist of a transverse vector component (Mt, 25a) in the x-y plane 80 and a residual vector component (z-component) aligned along the z-axis (Mz, 25b). The z-component Mz may be parallel or anti-parallel to the z-axis depending on the magnitude of the first angle $\theta 1$. As the ensemble is still exposed to the magnetic field B0, the transverse component Mt (and therefore the rotated magnetisation, M) precesses about the z-axis at the Larmor frequency. The magnetisation vectors shown in the drawings are drawn in the rotating frame of reference rotating at the Larmor frequency.

The desired first angle of rotation $\theta 1$ can be set by choosing an appropriate combination of duration and amplitude of a pulsed RF magnetic field B1a. As noted above, parts of the subject being scanned may affect the local strength of the RF magnetic fields (B1) at particular locations (spatial inhomogeneity) and cause the corresponding rotation angle at said locations to also be affected. This may result in up to a 50% variation in the actual rotation angle compared to the set angle, i.e. for a 90° rotation angle, this could result in an actual rotation between 45° and 135°.

The present inventor has identified that by exposing the subject to a second slice-selective RF magnetic field B1b that is configured to rotate the magnetisation about an orthogonal axis in the rotating reference frame (or in the case of circularly polarised RF magnetic fields, that is 90° out of phase with the first RF field B1a), portions of the subject where the rotation angle deviates from the set angle can be further rotated closer to or into the transverse plane. This is further explained in an exemplary embodiment with regard to FIG. 2c.

Figure 2C:
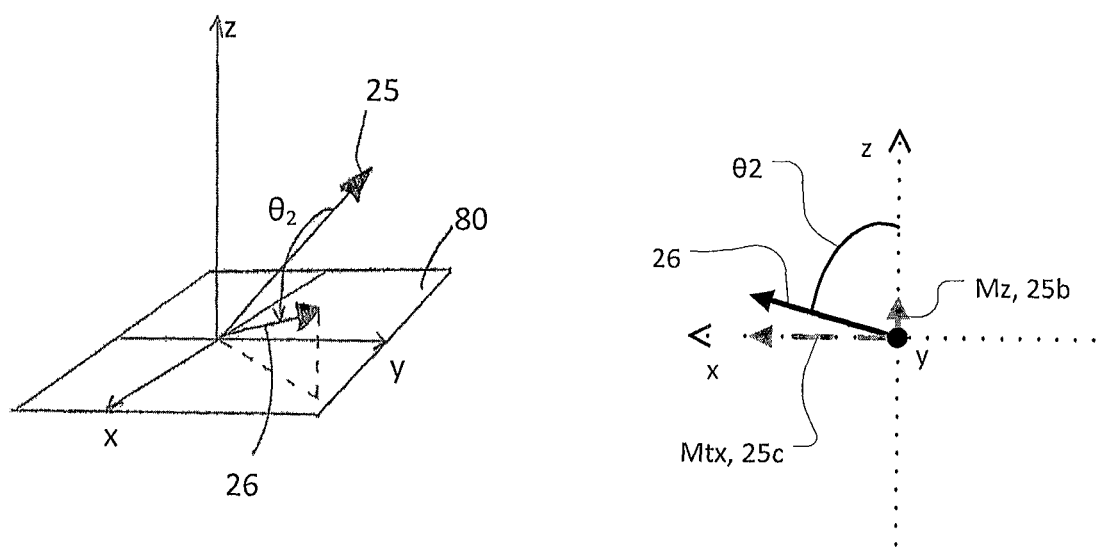
FIG. 2c illustrates a pair of vector diagrams, the leftmost being a three dimensional diagram, and the rightmost being a projection onto the x-z plane, each showing a second rotation of the net magnetisation when the ensemble of nuclei are excited by a suitable RF magnetic field.

As shown in FIG. 2c, the second RF magnetic field (B1b) excites the ensemble of nuclei to induce a second rotation of the rotated magnetisation M in orientation 25 about a second axis, in this example the y-axis (therefore orthogonal to the first axis), by a second angle (θ2) towards the transverse plane 80 to a second orientation 26.

The second rotation can be considered as only rotating the residual component of magnetization Mz 25b towards the transverse plane 80 as the transverse component Mt 25a is aligned with the y-axis. Notably, if the effect of the first rotation was to rotate the magnetisation by 90° into the transverse plane 80 then there is no further rotation by the second RF magnetic field.

The second angle θ2 can be selected in the same manner as the first angle. In a preferred embodiment, the second angle θ2 is set to be twice that of the first angle θ1. Importantly, the spatial inhomogeneity of the first RF magnetic field does not vary greatly with direction of the applied RF field and therefore will have the same effect on the second RF magnetic field B1b and therefore the corresponding rotation angle. The ratio between the first and second angles can therefore be set. For example, if the desired first and second angles are set at 90° and 180° respectively, and the first rotation angle was reduced to 45°, then the second rotation will be 90°. This still results in a magnetisation vector that is in the transverse plane. The same holds true if inhomogeneity causes over-rotation by 50% and results in first and second angles of 135° and 270°. Notably, the magnetisations are also rotated such that the phase differences (in terms of orientation between the components in the transverse plane) can be 45° from a single 90° rotation. Furthermore, the rotation following first and second angles of 135° and 270° results in a magnetisation that is 90° out of phase with something that was rotated by first and second angles of 45° and 90°.

If the resultant rotation at some portion of the subject is at other intermediate angles (i.e. between 45° and 135°) as is the case illustrated in FIGS. 2b and 2c, the resultant magnetisation vector after the two part rotation due to the first and second RF magnetic fields can be shown to still be close to the transverse plane. In other words, a larger component of the magnetisation vector is in the transverse plane compared to the residual component aligned with the longitudinal axis.

The resultant magnetisation at a given point in the slice, after a two part rotation where the ratio between first and second angle is 1:2 may not always be closer to the transverse plane than the situation where only one rotation is performed. However, the result from two part rotation is more uniformly close to the transverse plane over a larger range of angles than if only one rotation is performed. In this way, the two part rotation is less sensitive to inhomogeneity in the RF magnetic field B1. Simulated results illustrating the operation of an embodiment are shown in FIG. 3.

Figure 3:
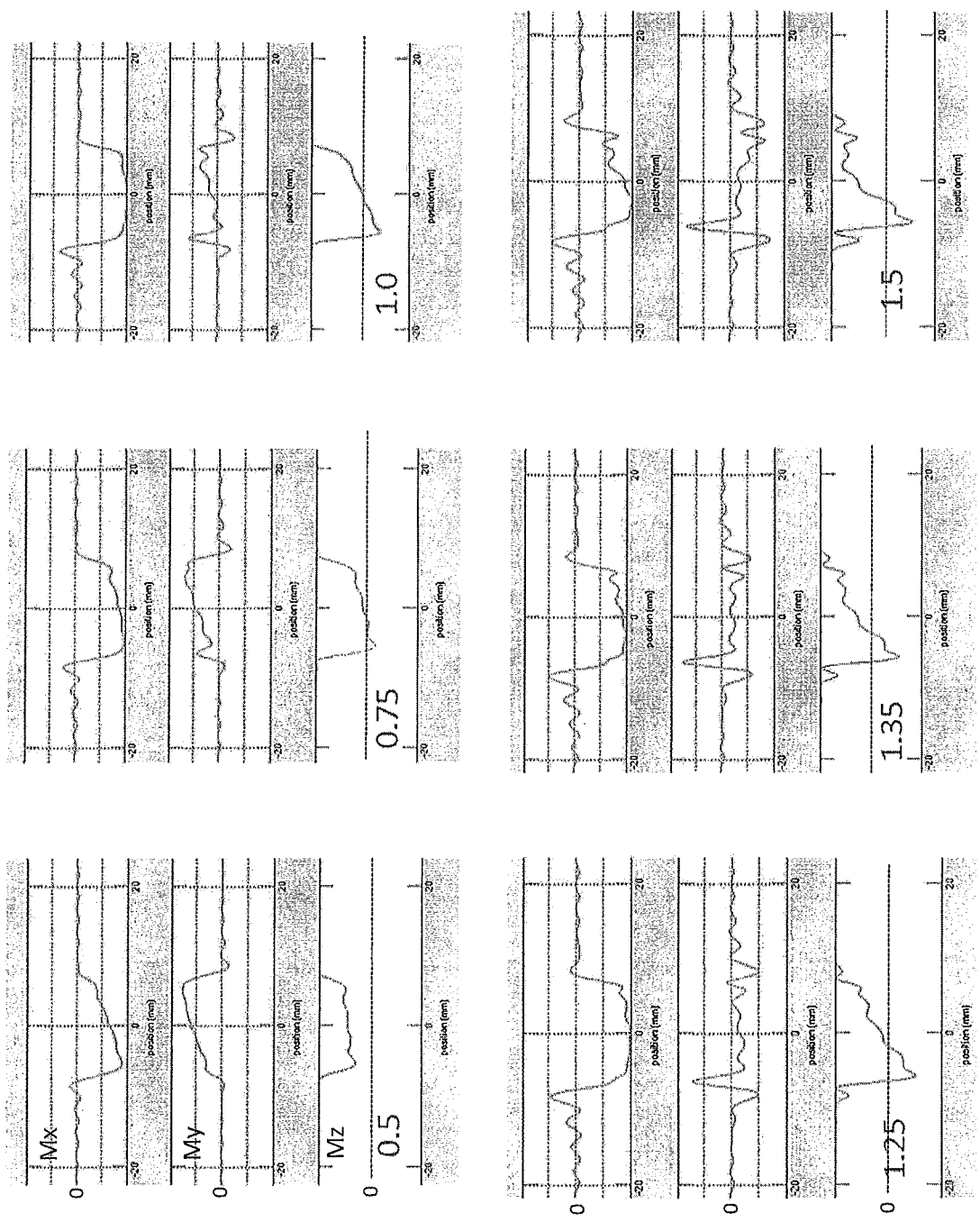
FIG. 3 is a plot of the magnitude of the residual magnetisation components along the x-, y- and z-axes for a range of first rotation/pulse angles.

FIG. 3 illustrates 6 groups of plots, with each group labelled 0.5, 0.75, 1.0, 1.25, 1.35 or 1.5. The numerical label given to each group (e.g. 0.5) indicates the extent of the influence of B1 inhomogeneity on the level of desired rotation illustrated in each group of plots. That is, the group of plots labelled 0.5 shows the simulated resultant magnetisation in the x direction (top plot—Mx), y direction (centre plot—My) and z direction (bottom plot—Mz) when the B1 inhomogeneity reduces the actual rotation caused by an MRI pulse to half of the intended (or desired) rotation. Similarly the plot labelled 1.5 shows the simulated residual magnetisation in the x, y and z direction when the local effect of B1 (caused by the B1 inhomogeneity) increases the actual rotation by 50% over that desired. In each case, the graphs illustrate the simulated residual magnetisation after a pulse containing two orthogonal slice selective rotations that have relative rotation of 0.8:1 e.g. 72°:90°. However, other relative rotation ratios may also work as discussed herein.

As can be seen in each of the six groups of plots, the residual magnetisation at the centre of the slice, i.e. the point on the plots where position (mm) is 0, is almost zero in the z direction (bottom plot), indicating that the resultant magnetisation is almost entirely in the x-y plane.

As can be appreciated by the person skilled in the art, the first and second rotation axes are preferably orthogonal.

Slice Selection

Figure 4:
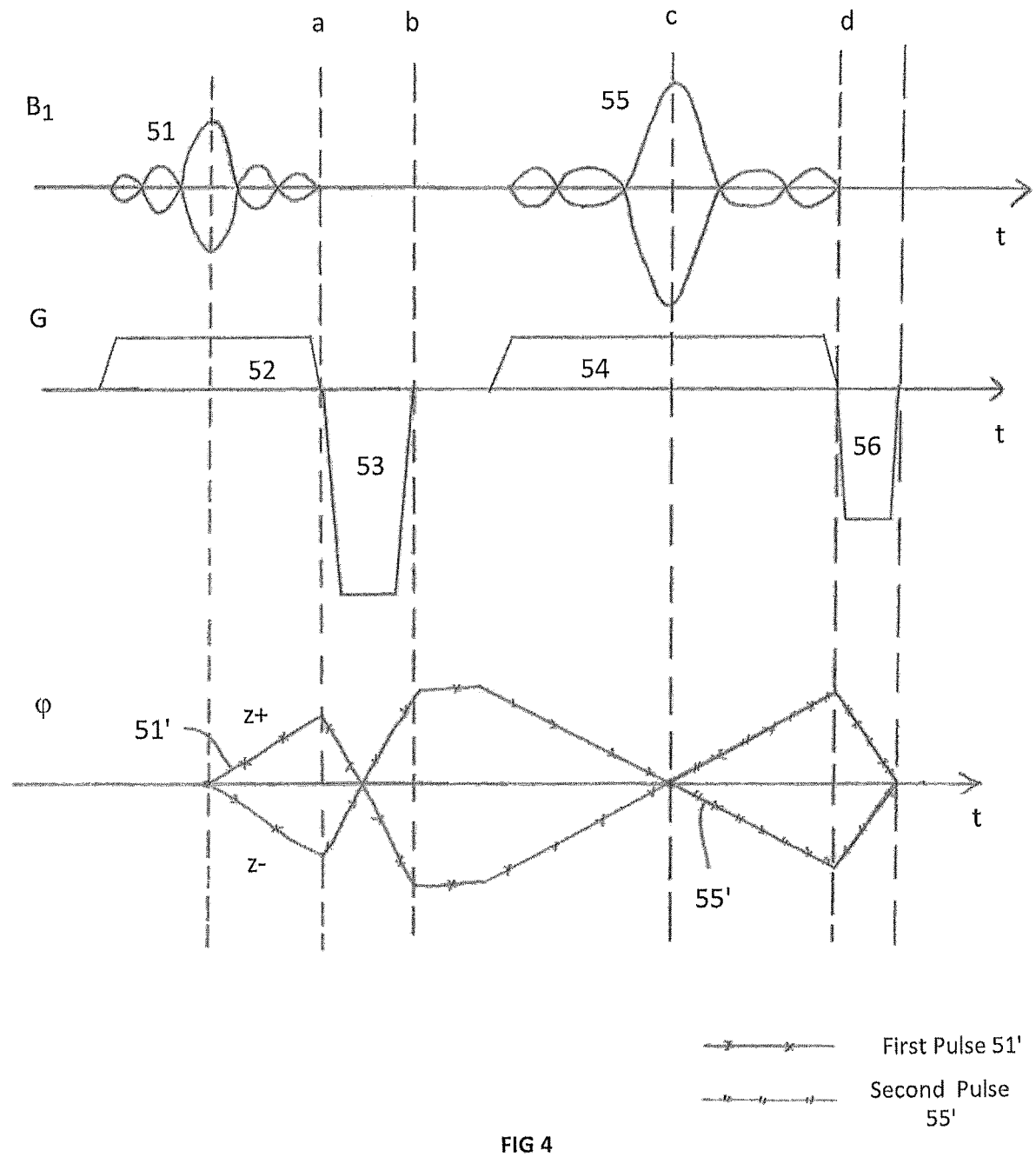
FIG. 4 is a plot of an exemplary MRI pulse sequence.
Figure 10:
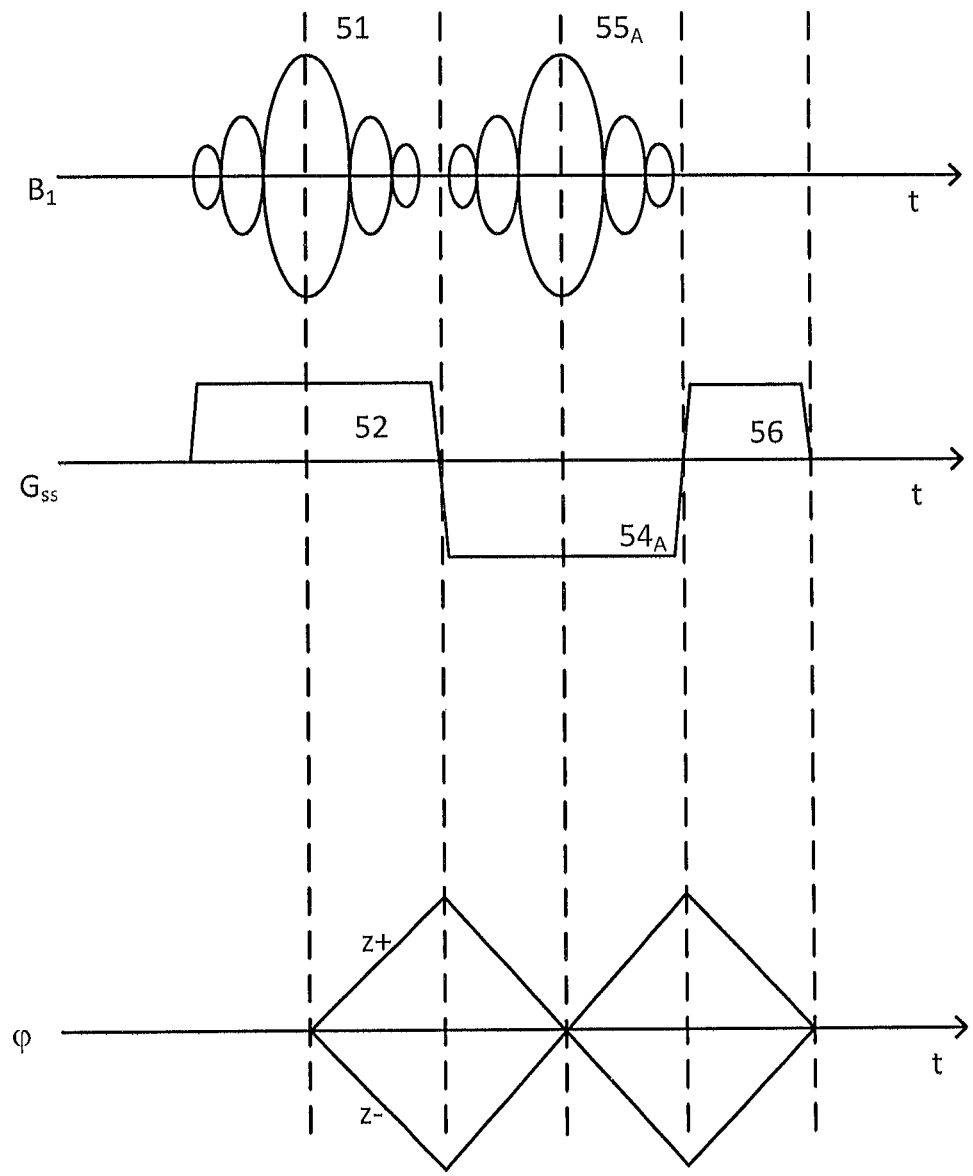
FIG. 10 illustrates another embodiment of an MRI pulse sequence according to an aspect of the present invention which uses a second slice selective gradient that performs re-phasing of spin vectors as well as slice selection.

In addition to the RF magnetic fields B1a and B1b, the MRI sequence includes a magnetic field gradient to perform slice-selective rotation. A time sequence of the amplitudes of the RF magnetic field and magnetic field gradients is shown in FIG. 4 and an alternative embodiment is shown in FIG. 10. The pulse sequence of FIG. 4 includes:

a first slice selective rotation, generated by first RF pulse 51 and corresponding first magnetic field gradient 52;

a second a slice selective rotation, generated by a second RF pulse 55 and corresponding second magnetic field gradient 54.

one or more phase adjustments; in this case being, a final re-phasing of de-phased magnetisations performed by application of a final re-phasing magnetic field gradient 56, and a first phase adjustment that is performed before the second slice selective rotation by application of a first re-phasing gradient 53.

In an exemplary embodiment where an axial cross-section is desired, a linear gradient along z is used so that the field at a position z is given by:

$$B_0(z) = |B_0| + G_z$$

Figure 5A:
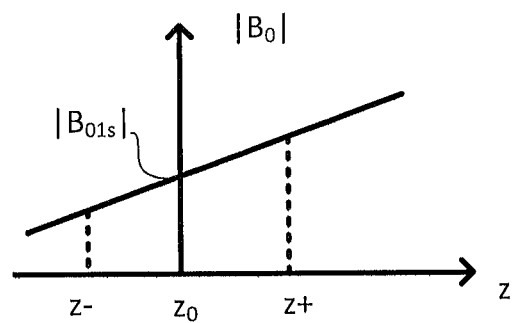
FIG. 5a is a plot of magnetic field strength as a function of position with gradient applied.
Figure 5B:
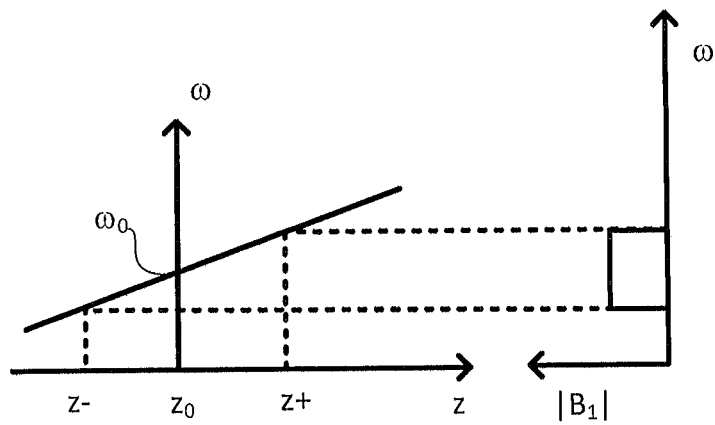
FIG. 5b is a plot of Larmor frequency as a function of position with gradient applied.

FIG. 5a shows the magnetic field strength B0 as a function of position along z with a positive magnetic field gradient G that varies along the z-direction. As can be seen, the magnetic field is higher at larger z and lower at smaller z and equal to the magnitude of B0 with zero gradient. As the Larmor frequency (ω) is proportional to the magnetic field strength, the Larmor frequency of nuclei in the portion of the subject exposed to the magnetic field gradient also varies along the z-direction (FIG. 5b). As is known in the art, the magnetic field gradient is used to select an axial slice of the subject (from Z− to Z+) to excite the nuclei therein with the transverse RF magnetic fields. In the embodiments described herein, only the nuclei within the slice are excited by RF magnetic fields B1a and B1b that cause rotation of the net magnetisation about x and y axes respectively. This is further explained below.

Slice selection is made possible by using RF magnetic fields that are amplitude modulated with functions known in the art to produce magnetic fields with a restricted bandwidth of frequencies. As an example, if the RF magnetic field is modulated as a 'sinc' function in time, the Fourier transform of this leads to a rectangular function in frequency. Therefore, RF magnetic fields with a finite bandwidth of frequencies over the range covered by the rectangular function can selectively excite a portion of the subject with a corresponding Larmor frequency within this frequency bandwidth (See FIG. 5b).

In this example the gradients applied at the time of the B1a and B1b fields have the same amplitude and B1a and B1b overlap in frequencies covered, the same selected slice of the ensemble of nuclei in the subject is excited by both B1a and B1b. As will be seen FIG. 10 shows an alternative approach in which the slice selection gradients provide a magnetic field that changes magnitude in opposite directions, that is one of the slice selection gradients has a positive gradient and the other a negative gradient.

As previously discussed, in a preferred embodiment, the second rotation angle is twice that of the first angle. This could be achieved if the pulse length of B1b is twice that of B1a, or the amplitude of B1b is doubled that of B1a, or a suitable combination of pulse length and amplitude adjustment is used. In other embodiments, B1a and B1b are either identical or the ratio of the B1a pulse length to the B1b pulse length can be any suitable ratio.

In practical embodiments, the RF magnetic fields are limited in time, commonly referred to as RF pulses. In preferred embodiments, the RF magnetic field is modulated as a time-limited sinc function (See FIG. 4). This can be considered a sinc function multiplied by a window function such as a Hamming, rectangular function or any known window function.

The person skilled in the art will appreciate that a magnetic field gradient G varying along different axes can be used to select slices in different orientations. For example G can vary along a transverse axis to produce sagittal or coronal slices of the subject.

Phase Adjustment

Figure 6A:
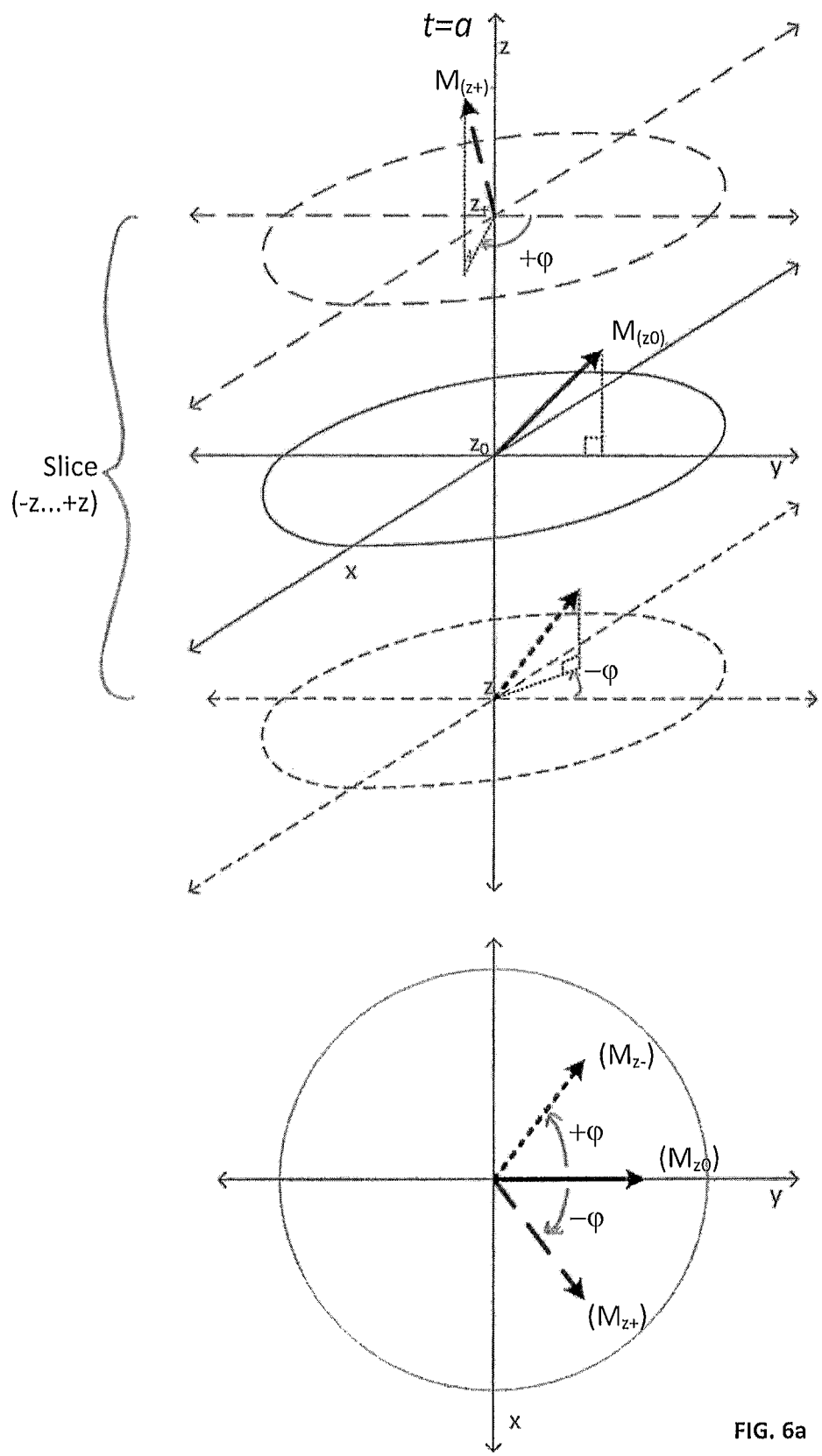
FIG. 6a illustrates a series of vector diagrams of the magnetisation at different z positions, denoted as $z_+$, $z_0$ and $z_-$, within a slice (where slice selection along the z-axis is being applied) after rotation by a first RF magnetic field to schematically illustrate dephasing that occurs at different z positions within the slice; a corresponding projection onto the x-y plane is also illustrated.

Any given group of nuclei exposed to the same magnetic field B can be described by a single net magnetisation vector M. As discussed earlier, the gradients do not alter the field direction but, as shown in FIG. 5b, the Larmor frequency varies with position when a gradient is present. After the first RF magnetic field B1a rotates the magnetisation vector M to orientation 25 the magnetisation vector M at a particular position along the z-axis precesses about the z-axis at the Larmor frequency corresponding to that position. According to FIG. 5b, the magnetisation vector at positions higher than position z0 ($M_{z+}$) will precess faster than the magnetisation at z0 ($M_{z0}$) due to the higher strength magnetic field B0 at that position along the z-axis. The magnetisation at lower positions ($M_{z-}$) precess slower than that at z0 due to the lower strength magnetic field B0. With reference to FIG. 6a, the result of gradient 52 is that the magnetisation vectors begin de-phasing with respect to the magnetisation at z0 during pulse 52. The amount of de-phasing can be quantified by a phase angle $\varphi$ between the magnetisation at either end of the slice with respect the magnetisation at z0. FIG. 6a illustrates a series of vector diagrams of the magnetisation at different z positions, denoted as $z_+$, $z_0$ and $z_-$, within a slice, after rotation by a first RF magnetic field to schematically illustrate dephasing that occurs at these three different z. A projection of the phases of $M_{z+}$, $M_{z0}$ and $M_{z-}$ is provided as the lower plot. FIG. 6a shows the magnetisation at time "a" during the MRI pulse sequence as shown in FIG. 4. As can be seen the phase at position z+ is advanced by a phase angle of $\varphi$ compared the phase at z0, indicated by +$\varphi$ on the topmost plot in FIG. 6a. Conversely the phase at position z− lags by a phase angle of $\varphi$ compared the phase at z0, and is indicated by −$\varphi$ on the lower plot of FIG. 6a.

As will be known by those skilled in the art it is important to re-phase the magnetisation vectors within the portion to obtain a larger MRI signal.

Figure 7:
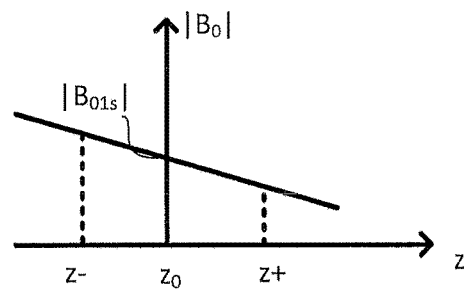
FIG. 7 is a plot of magnetic field strength as a function of position with a reversed polarity gradient applied.

The phase can be adjusted in a first phase adjustment. This can be achieved by applying a re-phasing gradient with a polarity that is reversed with respect to the first slice selection gradient. For example a re-phasing magnetic field gradient 53 as shown in FIG. 7 can be applied. The re-phasing gradient produces a lower strength magnetic field at higher positions along the z-axis and higher strength magnetic fields at lower positions.

Figure 6B:
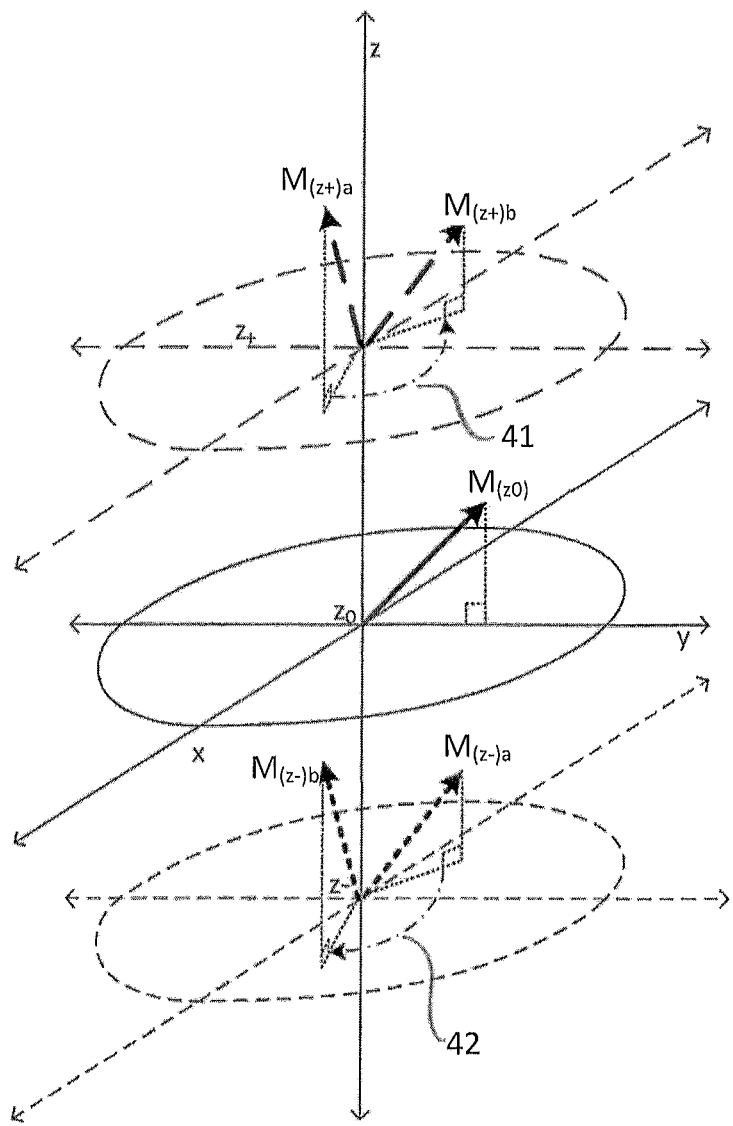
FIG. 6b is a series of vector diagrams corresponding to FIG. 6a but schematically illustrates the phase correction process across the width of the selected slice in the z direction.

FIG. 6b shows a series of vector diagrams corresponding to FIG. 6a but schematically illustrates the phase correction process across the width of the selected slice in the z direction. Approximate re-phasing occurs when this negative gradient has been applied for half the (time×magnitude) integral area of the gradient applied in conjunction with the first slice selection pulse. This completes the normal slice selection process. However, in accordance with some embodiments the phase correction process does not end when the phase at positions z+ and z− are the same as phase at z0 (i.e. when fully re-phased) but instead the phase is over corrected, such that the phase at position z+ lags by a phase angle of $\varphi$ the phase at z0, indicated by −$\varphi$ on the topmost plot in FIG. 6b, and also the phase at position z− leads by a phase angle of $\varphi$ compared the phase at z0, and is indicated by +$\varphi$ on the lower plot of FIG. 6b. Thus the phase at position z+ is retarded by 2$\varphi$ angle as indicated by reference number 41 and the phase at position z− is advanced by 2$\varphi$ angle as indicated by reference number 42.

Figure 6C:
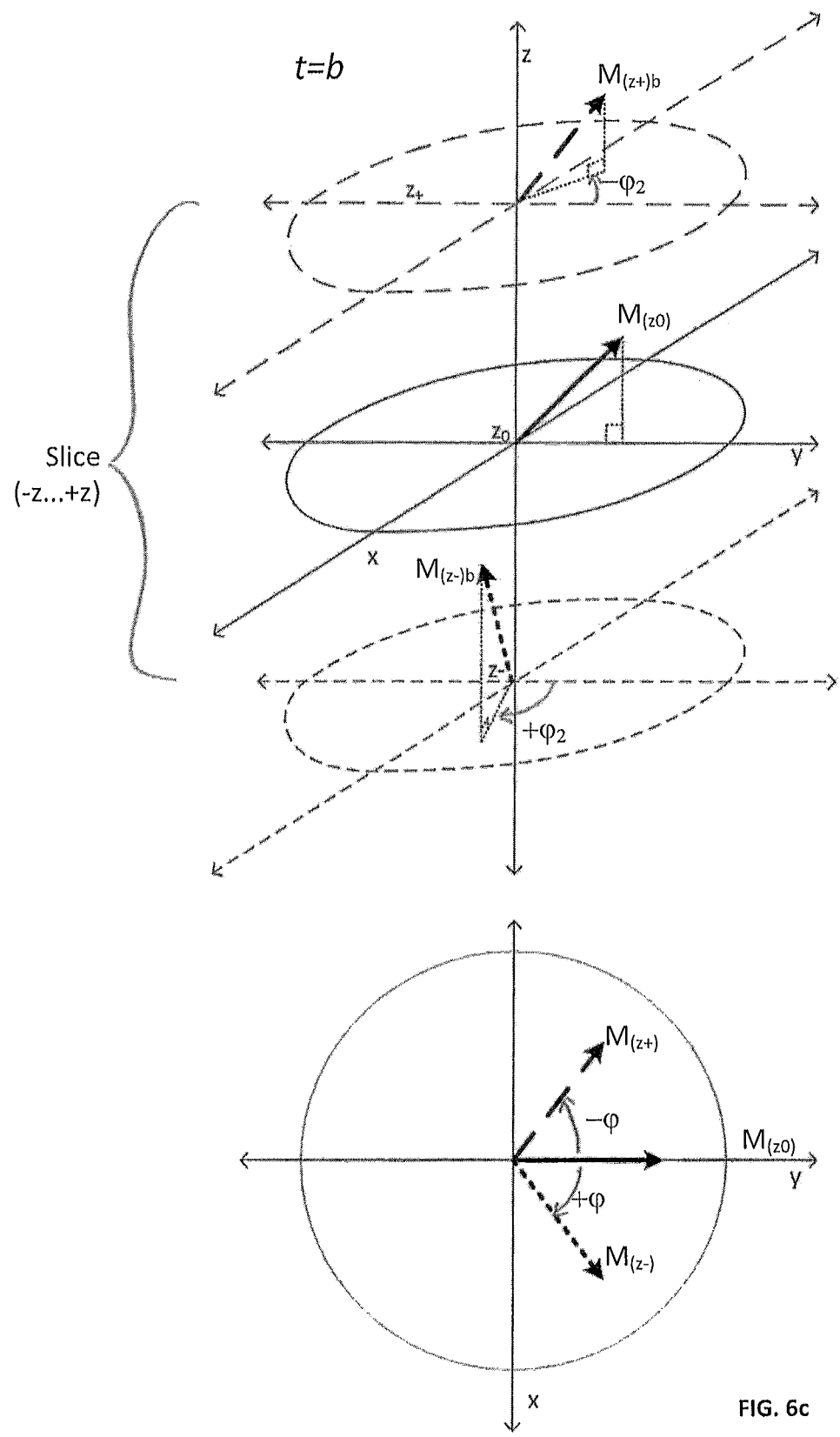
FIG. 6c illustrates a further series of vector diagrams of the magnetisation at different z positions within the slice and schematically illustrates the phases after the over-correction of phases within a slice by a first re-phasing gradient; a corresponding projection onto the x-y plane is also provided.

FIG. 6c illustrates a further series of vector diagrams of the magnetisation at different z positions within the slice and schematically illustrates the phases after the over-correction of phases. FIG. 6c illustrates the final phases of $M_{z+}$, $M_{z0}$ and $M_{z-}$ at locations z+, z0 and z− respectively. The magnetisation vector Mz+ (at positions higher than position z0) now precess slower than the magnetisation at z0 and the magnetisation M− (at lower positions) precess faster than that at z0. A corresponding projection onto the x-y plane is also provided;

At some time during the application of the second slice-selection gradient 54, the magnetisation may be, or be close to being, completely in-phase. However during the second slice-selective rotation they will again de-phase.

Accordingly, following the second slice-selective rotation of the magnetisation by the second RF magnetic field 55 (B1b), the magnetisation at different z positions are again de-phased. A final phase adjustment is applied by using a reversed gradient in a final re-phasing magnetic field 56 to correct the de-phasing within the ensemble. This final phase adjustment is applied to re-phase the magnetisation vectors within the ensemble so that they are in-phase to maximise the MRI signal.

The lower plot of FIG. 4, illustrates the phase of the magnetisation vectors at positions higher (z+) than z0, and the phase of the magnetisation vectors at positions lower (z−) than z0, as a function of time to illustrate schematically the evolution of phase during the application of the pulse sequence. The phase evolution can be represented by a plot in which phase effectively originates from zero at the middle of any RF pulse element, where the final phase accumulated after successive gradient pulse elements is accumulative. Re-phasing of the signal excited across the selected slice occurs at all points where the net phase is zero.

In the lower plot of FIG. 4 the phase evolution generated by the first slice selective pulse 51 is indicated by reference number 51' and shown in the lower plot marked with crosses. The second RF pulse 55 and rephasing gradients 53 and 56 each affect their own signals that evolve from the centre of each pulse. The phase evolution of the second RF pulse 55 is labelled by reference numeral 55' shown in the lower plot marked with paired dashes. Thus the two component RF pulse sequence of the present embodiment thus excites two signals, both of which provide maximum signal at a subsequent point in time when the net phase accumulation from both signals are simultaneously zero. The phases of the signals are along the x- and y-transverse directions as effected by the different phases of the two pulses (x- and y-) so that the net signal has a phase formed by the vector-sum of the two components.

In the embodiment shown in FIG. 4, the first re-phasing gradient 53 has a larger amplitude than the first slice-selective gradient 52. Also, the integral of the amplitude of the first magnetic field gradient 52 over time is equal to the integral of the amplitude of the first re-phasing magnetic field gradient 53 over time. In some embodiments, the first re-phasing gradient also has a shorter duration than the first slice-selective gradient.

Figure 8A:
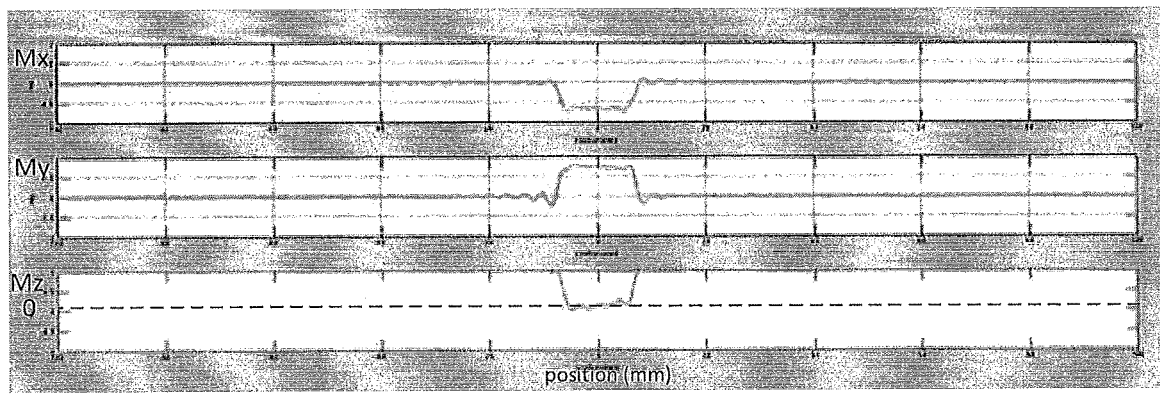
FIG. 8a illustrates three plots showing the residual magnetism in each of the x, y and z directions using an embodiment of the present invention.

It should be noted that the figure is schematic insofar as it does not show the precise shape of the phase evolution curve over time and all slice-selective signal excitation pulses have a non-symmetric gradient profile since they must contain the extra-refocusing element required to account for magnetization evolution during the RF period. In a preferred embodiment, the ratio between the magnitude of the first re-phasing magnetic field gradient is above 2 and typically between 2.02 and 2.04 times the magnitude of the first magnetic field gradient. In a most preferred embodiment, the ratio between the magnitude of first re-phasing magnetic field gradient and the first magnetic field gradient is 2.03. The final orientations of the net magnetisation at different positions along the z-axis after a MRI pulse sequence in accordance with the disclosed invention have been calculated by solving the Bloch equations and shown in FIG. 8a. A ratio of 2.03 was used for the calculation. The plot shows the magnitude of the components of the final magnetisation along each orthogonal axis. Although there is some variation at different positions along the z-axis, the residual component aligned with the z-axis is very small compared to the components aligned with the x and y axes. As the x and y components have a similar magnitude at different positions along the z-axis, the plot also indicates that the de-phased magnetisations are now mostly in-phase and the de-phasing has been largely corrected. That is, FIG. 8a shows that at all positions along z, the magnetisation is close to or at a 45° angle between the x and y axis. This phase correction is largely due to the selection of a ratio of 2.03 between the magnitude of first re-phasing magnetic field gradient and the first magnetic field gradient.

Figure 8B:
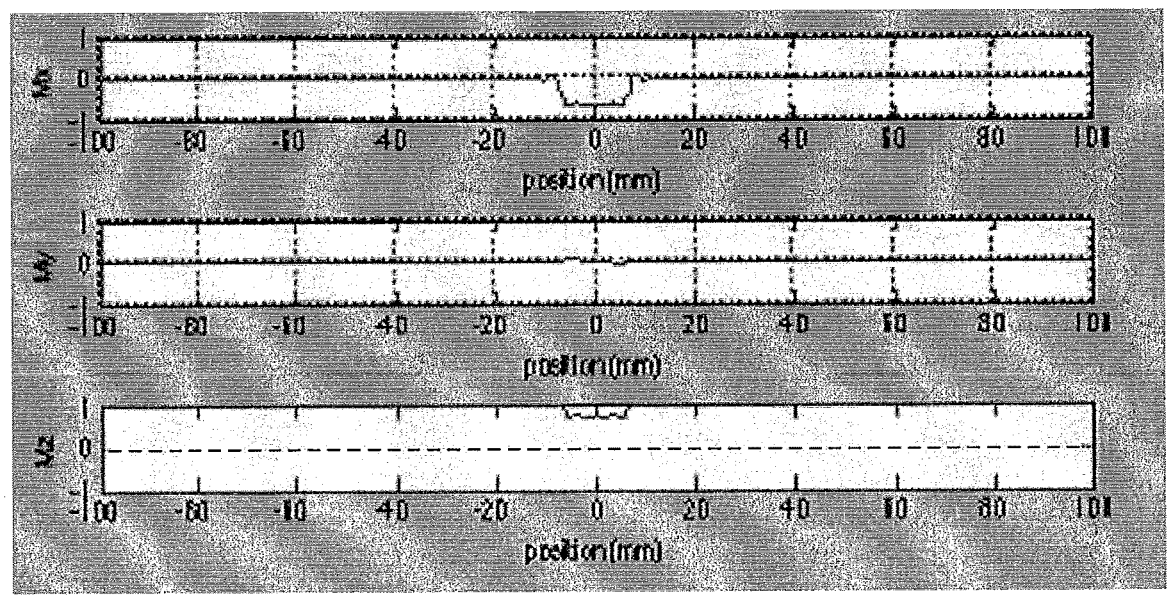
FIG. 8b illustrates three plots showing the residual magnetism in each of the x, y and z directions as a result of a single 45° rotation.

As a comparison to the result of the MRI sequence described above, FIG. 8b shows the result of a single 45° rotation. This illustrates the result of an inhomogeneity reducing the rotation angle of an intended single 90° rotation by 50%. It can be seen in FIG. 8b that there is a still a significant magnitude to the Mz component.

Figure 9A:
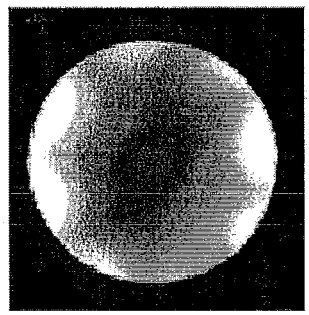
FIGS. 9a to 9e illustrate results using an embodiments of the present invention.
Figure 9B:
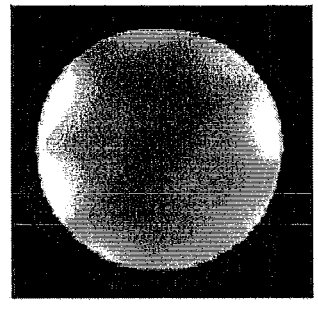

FIGS. 9a to 9e illustrate additional results using embodiments of the present invention. Specifically FIG. 9a illustrates a gradient echo MRI of a uniform spherical phantom using a standard 90° sinc pulse. As can be seen the signal level varies greatly across the slice, and has a distinct dark central patch. The bright scalloped edges correspond to local inhomogeneity caused in areas near to the transmit coils. FIG. 9b illustrates an image of the same phantom using a 1-2 pulse sequence, such as that illustrated in FIG. 4. In the pulse used a first 45° slice selective rotation in the x direction is followed by a second 90° slice selective rotation in the y direction. As can be seen qualitatively the image in FIG. 9b is more uniform than that of FIG. 9a.

Figure 9C:
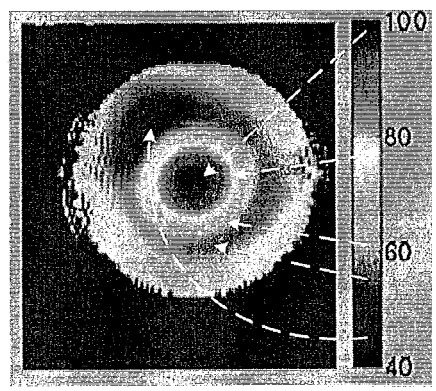
Figure 9D:
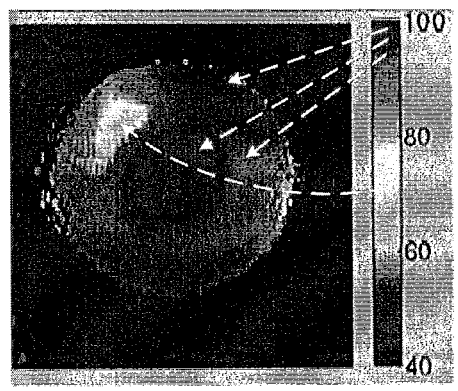
Figure 9E:
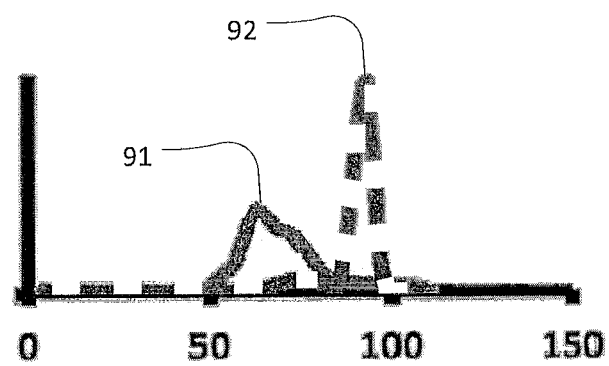

FIGS. 9c and 9d illustrate RF flip angle maps corresponding to FIGS. 9a and 9b. In each figure, the arrows indicate a correlation between the flip angle scale on the right and shading in the RF flip angle map. As can be seen, in FIG. 9c, the flip angle in the centre of the phantom are past 90 degrees, and is surrounded by a ring of flip angles of 60 degrees and below. In FIG. 9d the flip angles are far more uniform and the vast majority sit in a narrow angular range about the desired 90°. This view is further supported by FIG. 9e which illustrates the flip angle distribution for the conventional 90° sinc pulse (solid blue, labelled 91) and equivalent 1-2 pulse sequence (dashed, red line, labelled 92). The improved flip angle homogeneity can be seen in 9e by the tightness of the histogram at 90 degrees in the red plot 92 belonging to the 1:2 pulse sequence.

As will be appreciated by the person skilled in the art, if different RF magnetic field pulses are used or gradients with different durations are used, the optimal ratio between the magnitude of first re-phasing magnetic field gradient and the first magnetic field gradient to ensure that the magnetisation are in-phase at the end of the MRI pulse sequence may differ.

FIG. 10 illustrates another exemplary MRI pulse sequence. This differs from the previous embodiment in that instead of applying a re-phasing gradient between the two slice selective rotations, the second gradient selected for the second slice selective rotation is arranged to perform the re-phasing role as described below.

This MRI pulse sequence begins with a first radio-frequency magnetic field pulse (151) and a corresponding first magnetic field gradient 52 that are used to excite nuclei within a part of a subject to perform a first slice-selective rotation.

As noted above this first radio-frequency magnetic field pulse rotates a net magnetisation vector, about a first axis (e.g. the x axis) such that a portion of the magnetisation now lies in along the y axis. As with the previous example the first slice selection gradient 52 is a magnetic field that has a magnitude that increases along direction that is transverse to the slice being imaged. For convenience this is deemed to be a positive gradient.

Next a second radio-frequency magnetic field pulse (55A) and corresponding second magnetic field gradient MA is used to cause a second slice-selective rotation. As with the previous embodiment this pulse and slice selection gradient cooperate to rotate the net magnetisation about a second axis (the y axis in this example) such that any residual magnetisation that existed along the z axis is rotated into the x-y plane. Where this embodiment differs from the previous embodiment is that the second slice selection magnetic field gradient 54A has a negative gradient compared to the first slice selection gradient. That is, the magnetic field caused by the second slice selection gradient decreases along the direction in which the first slice selection gradient increases. This means that as well as enabling slice selection the gradient causes at least partial re-phasing of the magnetisation vectors that were de-phased (as illustrated in FIG. 6a) by the first slice selective rotation process.

As will be appreciated the first and second positive and negative gradients will need to be created so that the slices formed by each gradient are in registration with each other. This may require the second RF pulse to have a negative frequency offset applied to so that the slice centres align along direction of the B0 field. This allows slices offset from the centre of the magnet to be excited.

Finally, the pulse sequence includes final re-phasing magnetic field gradient to correct de-phasing of the magnetisation vectors within the ensemble that are a result of the second slice-selective rotation. Final re-phrasing magnetic field gradient in this case consists of a positive gradient of approximately half the duration of the gradient applied in the previous slice selection gradient segment but equal size, as shown in FIG. 10.

FIGS. 9 to 20 illustrate a series of embodiments that include additional slice selective rotations. In these examples three slice selective rotations are used to achieve a desired rotation angle that is relatively insensitive to B1 field inhomogeneity. In these examples the magnetisations are assumed to make clockwise rotations. It will be appreciated however that the methods disclosed herein can be applied, mutatis mutandis, to atoms whose magnetisations make anti clockwise rotations.

Figure 11:
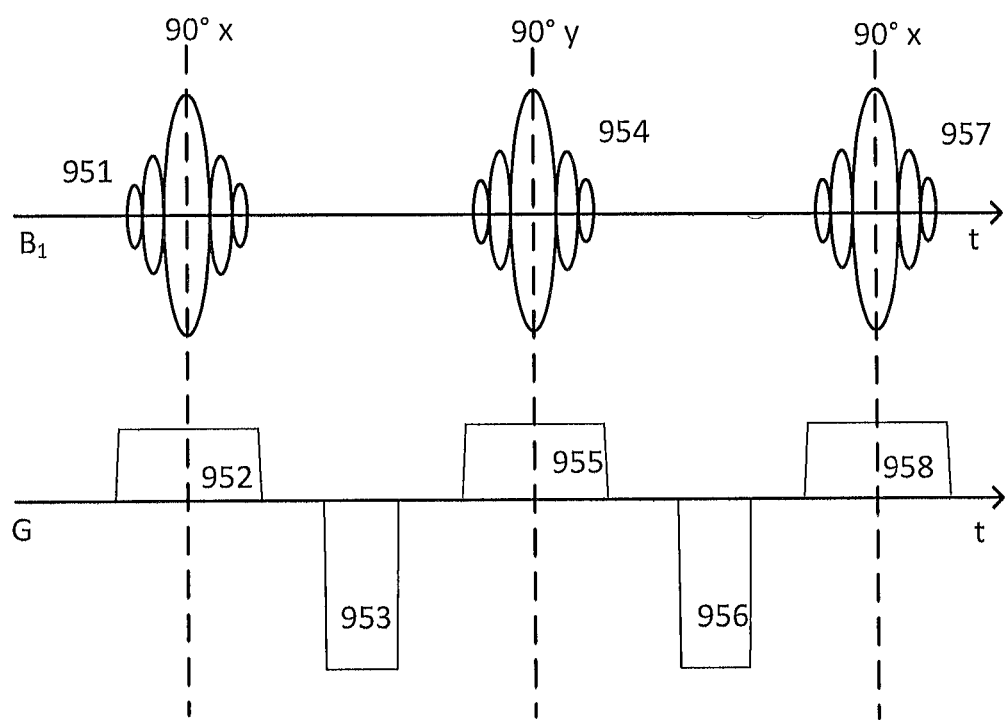
FIG. 11 illustrates another embodiment of an MRI pulse sequence according to an aspect of the present invention that uses three pulses in two axes of rotation to generate a slice selective 180 degree refocussing pulse or an inversion pulse when the initial magnetisation starts along the +z axis.

Turning firstly to FIG. 11, which illustrates a pulse sequence for achieving a rotation equivalent to a slice-selective 180 degree refocussing pulse or an inversion pulse. In this example this is provided by applying three successive 90 degree rotations and each rotation is applied orthogonally to each previous rotation. In FIG. 11 the top plot represents the RF magnetic field pulses B1, which in this example are shaped as sinc pulses. The lower plot illustrates applied magnetic field gradients.

For the refocussing pulse the magnetization is assumed to start in the x-y plane and must be "flipped-over" along an axis. This is illustrated schematically in FIGS. 12a to 12d by the rotational motion of the disk 900. As can be seen the disk 900 is shown as initially lying in the x-y plane as it represents a multiplicity of magnetisations lying in that plane but covering a range of phases. The disk is shown to have a top surface 901 (shaded grey) and a bottom surface 902 (shaded white and not seen until FIG. 12d). Datum points are also illustrated to assist in visualisation of the three dimensional motion of the disk 900. These dots include a single white dot initially (in FIG. 12a) adjacent the +y axis, a single black dot initially adjacent the –y axis. Both single dots are at a positive x-position. A pair of adjacent dots are also shown. The pair comprising a white dot in the +y side of the +x axis, and a black dot in the –y side of the +x axis.

Figure 12A:
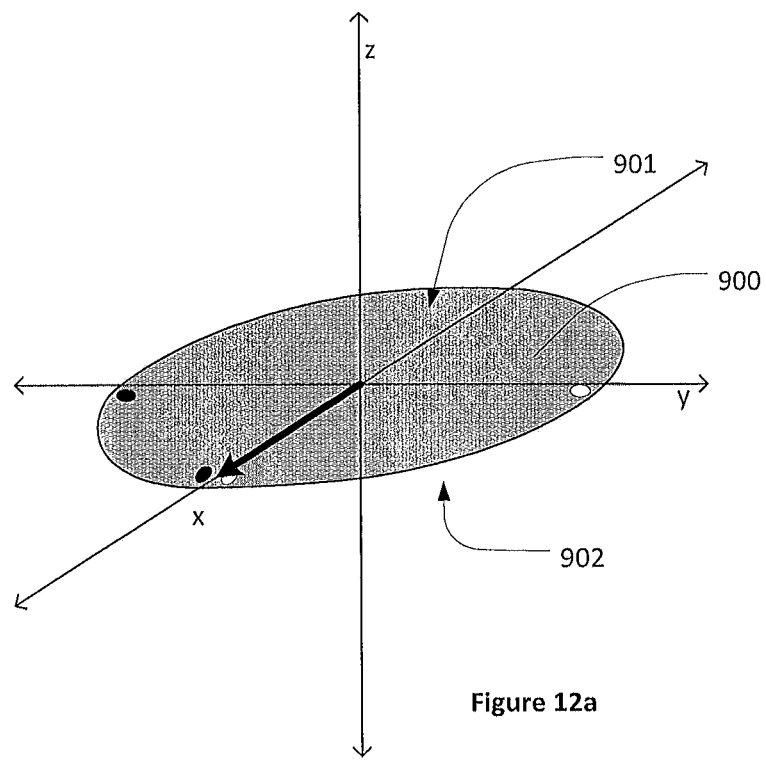
FIGS. 12a to 12d schematically illustrate the rotations of the net magnetisation when the pulse sequence of FIG. 11 is used as a slice selective 180 degree refocussing pulse.
Figure 12B:
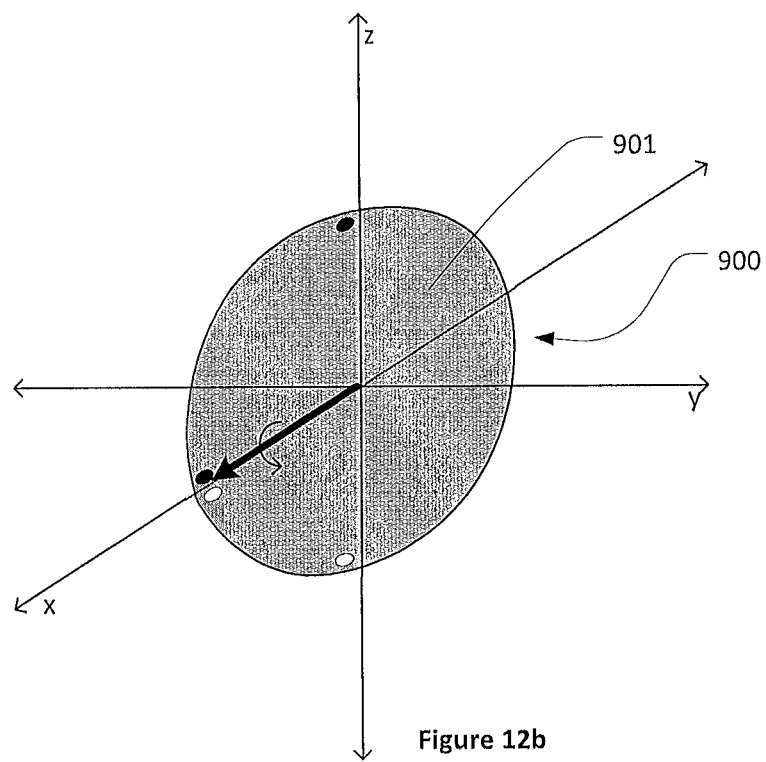

The pulse sequence illustrated on FIG. 11 begins with a slice selective rotation generated by the application of a first RF magnetic field pulse 951 and an associated corresponding magnetic field gradient 952. The magnetic field gradient has a magnitude that increases along a direction transverse to a slice being selected. The slice selective rotation 951 is configured to generate a 90 degree rotation (i.e. has a desired rotation of 90 degrees) in the positive direction about the x axis. The rotation produces is shown in FIG. 12b. As can be seen the disk 900 has rotated about the x axis as that it now lies in the x-z plane and no y magnetisation.

Next a rephasing gradient 953 is applied with a reversed gradient direction to the first slice selection magnetic field gradient 952. The re-focussing magnetic field gradient 953 is generated to re-phase the de-phased gradients generated by the first slice selective rotation.

Figure 12C:
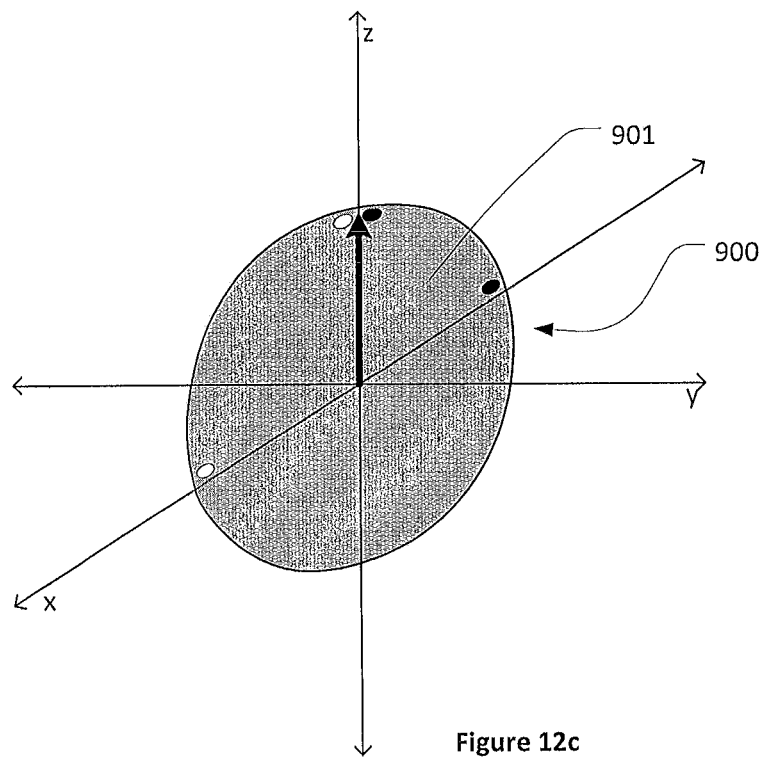

Then a second slice selective rotation is generated by the application of a second RF magnetic field pulse 954 and an associated corresponding second magnetic field gradient 955. The magnetic field gradient has a magnitude that increases along a direction transverse to a slice being selected. The slice selective rotation 954 is configured to generate a 90 degree rotation in the positive direction about the Y axis. The rotation is illustrated in FIG. 12c. As can be seen, as the disk rotates the pair of datum dots are now located adjacent the +z axis.

Next a rephasing gradient 956 is applied with a reversed gradient direction to the second slice selection magnetic field gradient 955. The re-focussing magnetic field gradient 956 is generated to re-phase the de-phased gradients generated by the first slice selective rotation.

Figure 12D:
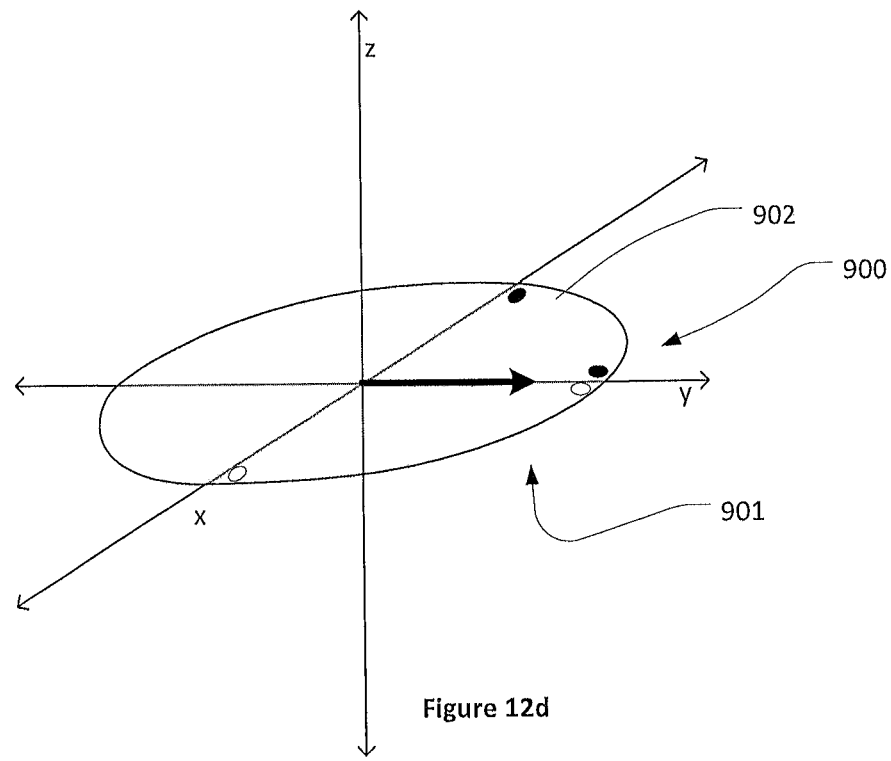

Then a third slice selective rotation is generated by the application of a third RF magnetic field pulse 957 and an associated corresponding third magnetic field gradient 958. The magnetic field gradient has a magnitude that increases along a direction transverse to a slice being selected. The third slice selective rotation 957 is also configured to generate a 90 degree rotation in the positive direction about the x-axis. In this example the third slice selective rotation is generated by application of an RF magnetic pulse and gradient field that are essentially the same as those used in the first slice selective rotation. As shown in FIG. 12d this causes the disk 900 to flip over so that side 902 is now on the side of the positive z axis and the pair of datum dots are now adjacent the positive y axis.

As can be seen the associated gradient waveform is symmetric, just like in the standard 180° refocusing pulse; the extra re-phasing gradient lobe not being required since the magnetization starts in the x-y plane and not along the z-axis. Note all three pulses are 90° and the signal excited by the first pulse effectively experiences zero phase from the subsequent four gradient lobes.

Figure 13A:
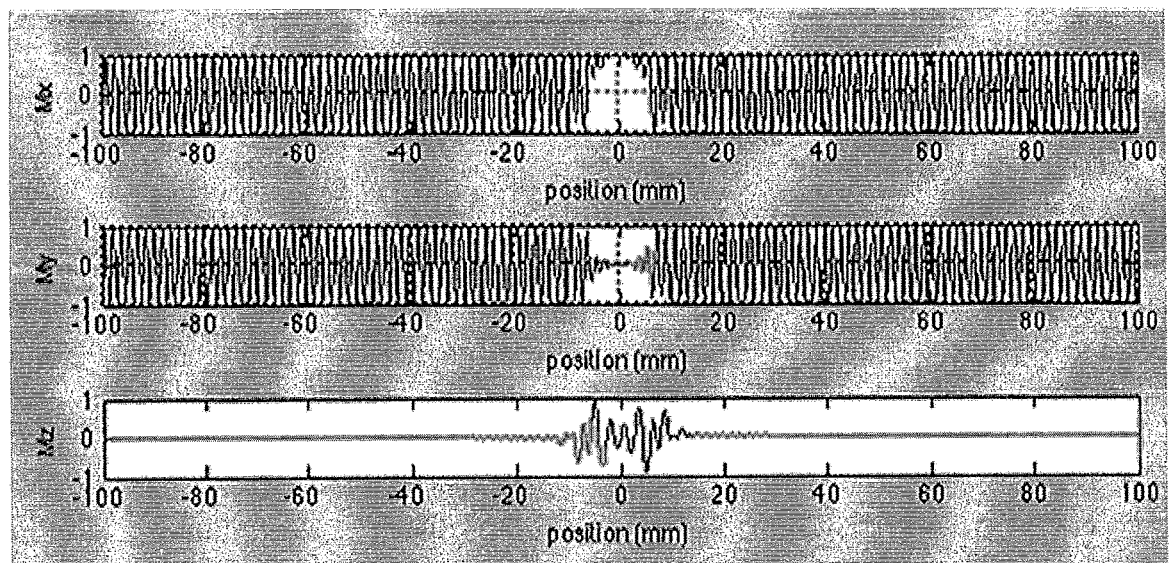
FIGS. 13a and 13b respectively illustrate a simulation of the operation of a conventional 180 degree refocussing pulse (FIG. 13a) and a simulation of the operation of a pulse sequence of FIG. 11 (FIG. 13b).
Figure 13B:
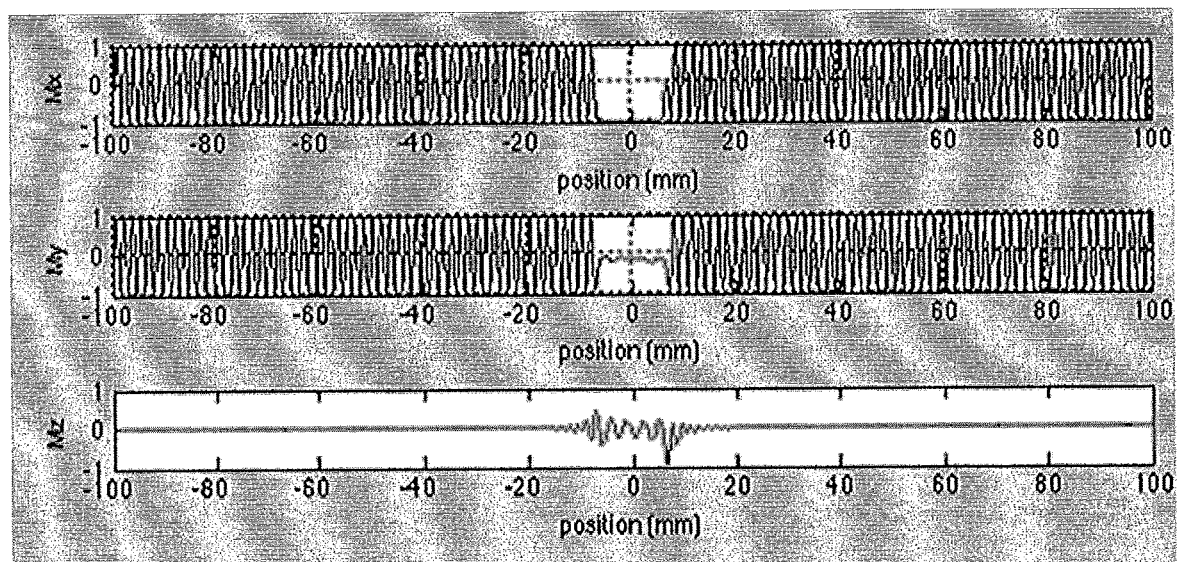

FIGS. 13a and 13b illustrate simulations of the Bloch equations for a conventional 180 degree refocussing pulse in (FIG. 13a) and that produced by the 180 degree refocussing pulse sequence of FIG. 11. As can be seen, in FIG. 13a the resultant magnetisation predominately lies in the Mx direction. However the slice shape in the x and y directions is significantly compromised away from the slice centre, and significant magnetisation still exists at some values of z. In FIG. 13b simulations for the pulse sequence of FIG. 11 are shown. As can be seen the response in the x and y directions are more rectangular (i.e. the slice has a more defined flat bottom and more "upright" clear cut-offs at their sides. Much less signal remains in the z direction also.

Figure 14A:
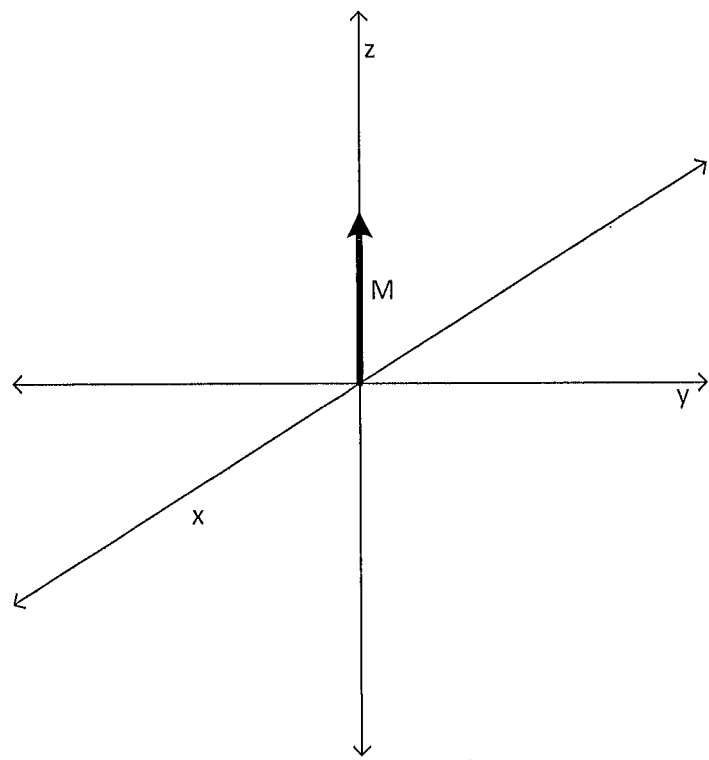
FIGS. 14a to 14d schematically illustrate the rotations of the net magnetisation when the pulse sequence of FIG. 11 is used as an inversion pulse.
Figure 14B:
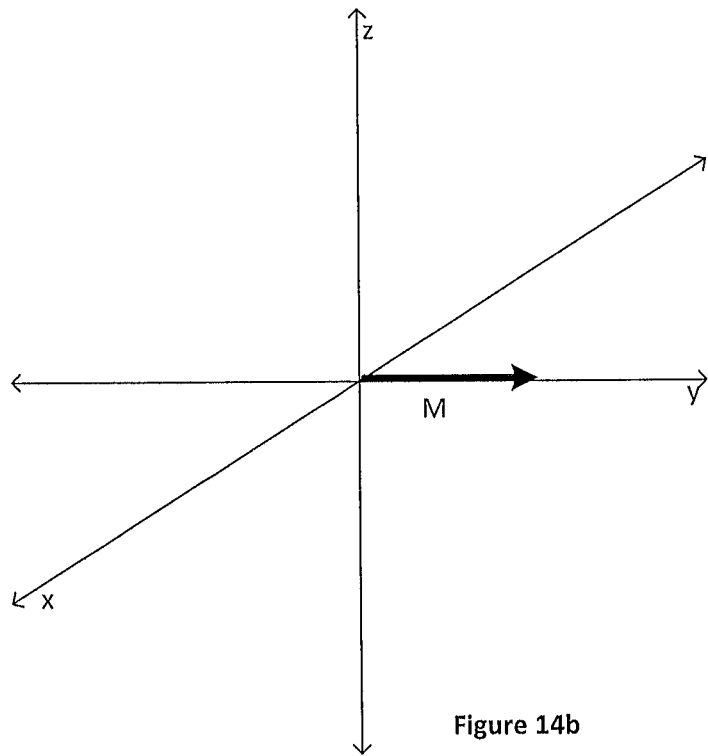
Figure 14C:
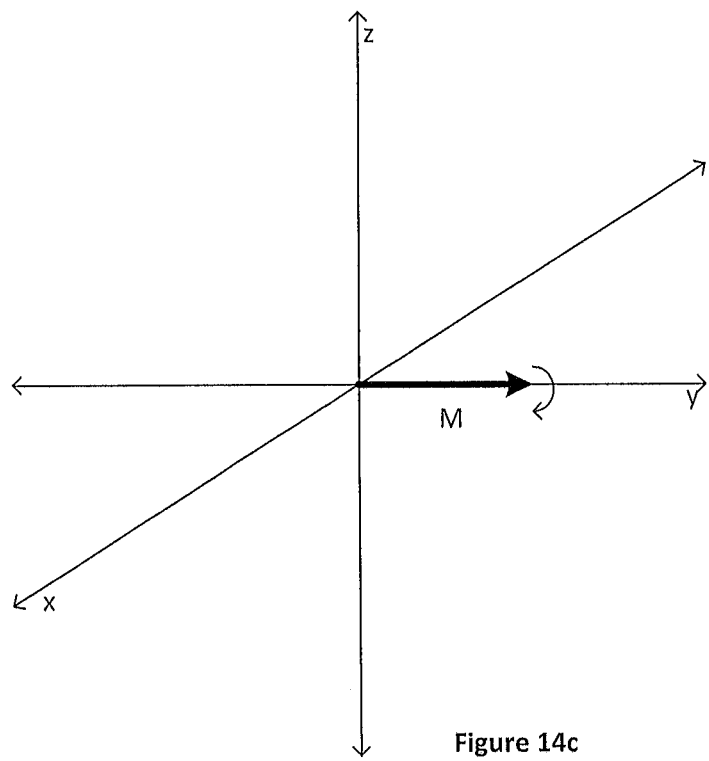
Figure 14D:
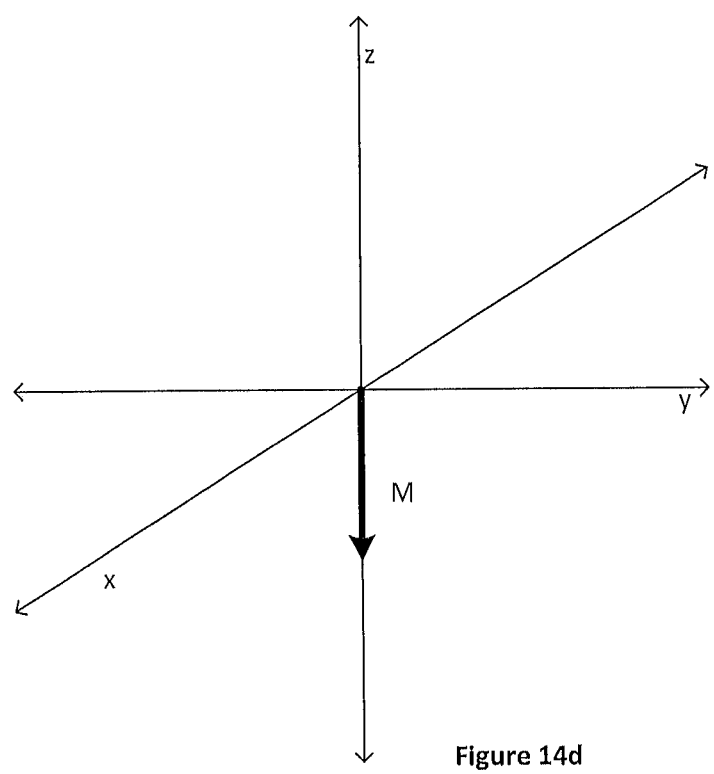

As noted above this same pulse sequence can be used as a slice selective 180 degree inversion pulse for a z-magnetisation. The rotation of the net magnetisation in this case is illustrated in FIGS. 14a to 14d. Initially in FIG. 14a the net magnetisation M is aligned along the positive z axis. The first slice selective rotation moves it into the position shown in FIG. 14b in which M lies along the positive y axis. After re-phasing the magnetisation M is rotated about the y axis, which does not cause any net movement of the magnetisations M. After the final re-phasing the magnetisation is rotated again in the positive x-direction by 90° and, as shown in FIG. 14d ends up aligned along the negative z axis.

Figure 15:
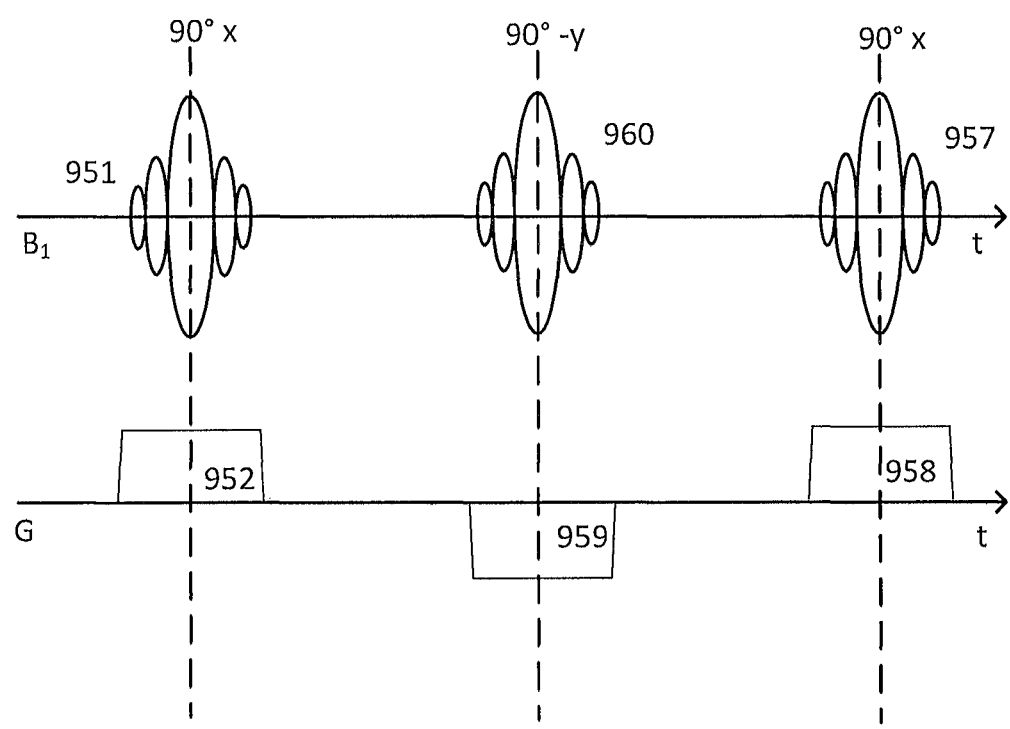
FIG. 15 illustrates an alternative MRI pulse sequence equivalent to that of FIG. 11, but which uses no dedicated re-focusing gradients.

FIG. 15 illustrates an alternative MRI pulse sequence equivalent to that of FIG. 11, in that it is intended to produce the same effect as a 180 degree re-focussing pulse, but which uses no dedicated re-focussing gradients. As disclosed in connection with the previous embodiment the pulse sequence includes first and third slice selective rotations comprising respective RF magnetic field gradients 951, 957, and corresponding slice selection gradients 952 and 958. However, in a manner analogous to FIG. 10, the pulse sequence of FIG. 15, inverts the direction of the slice selection gradient 959 used for the second slice selective rotation, so that it may also serve to perform refocussing. Furthermore the second RF magnetic field pulse 960 is applied with a negative phase when compared to the second RF pulse 954 of FIG. 11. Furthermore the second radio frequency magnetic pulse is also applied with a negative phase compared to the 2nd RF pulse in the first embodiment. That is, the RF magnetic field B1b, in the case of circularly polarised RF magnetic fields, is −90° out of phase with the first RF magnetic field B1a.

Also as mentioned in relation to FIG. 10, the multiple slice selective gradients will need to be performed so that their slices are in registration with each other so appropriate frequency offsets will need to be applied to them so that they correctly align along the B0 field.

Figure 16A:
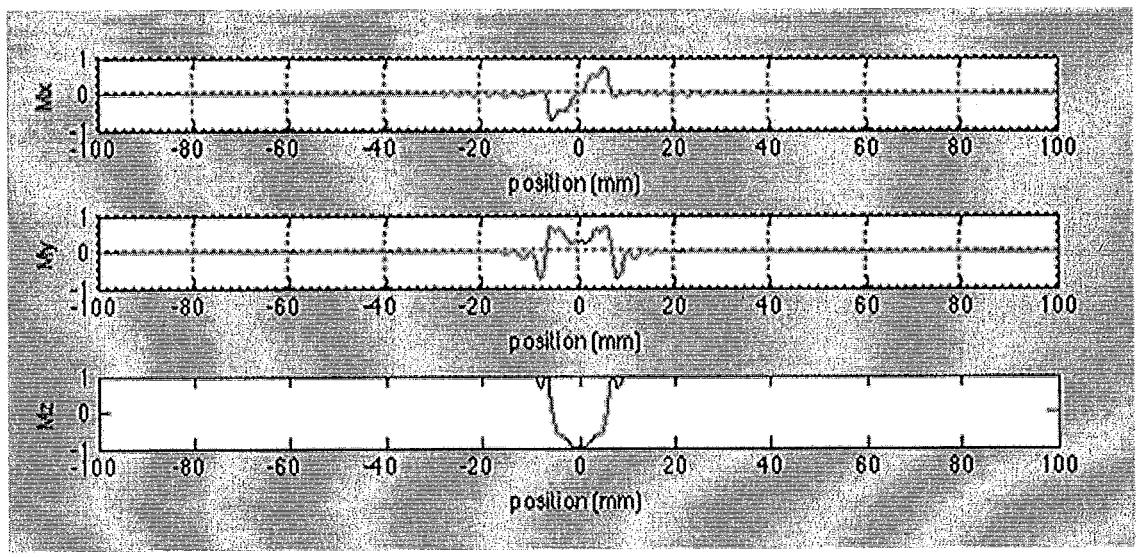
FIGS. 16a and 16b illustrate simulations of the operation of a conventional inversion pulse (FIG. 16a) compared to that of the 180 degree inversion pulse (FIG. 16b) sequence of similar structure to that of FIG. 11.
Figure 16B:
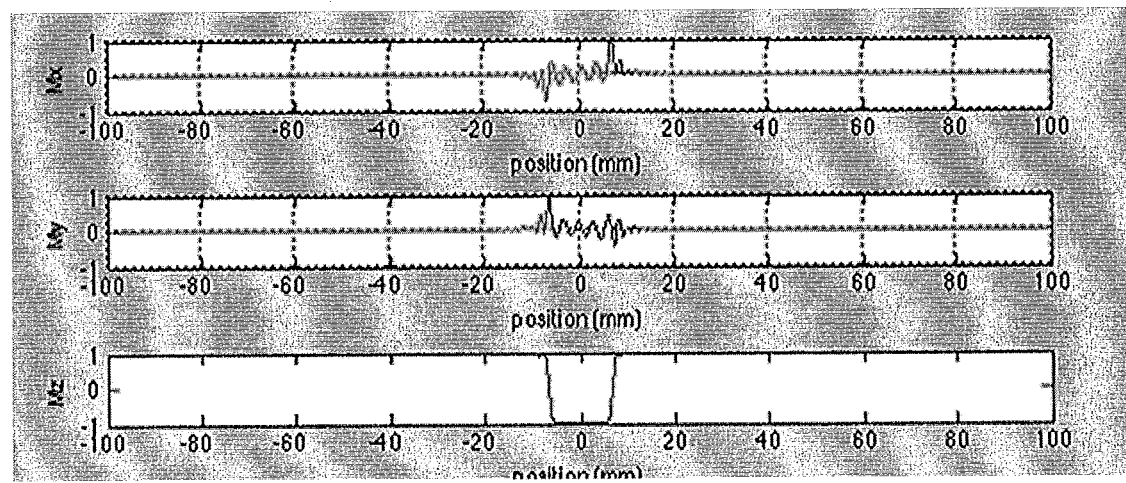

FIGS. 16a and 16b illustrate simulations of the Bloch equations for a conventional 180 degree inversion pulse in (FIG. 16a) and that produced by the 180 degree inversion pulse sequence of FIG. 11(FIG. 16b).

Figure 17:
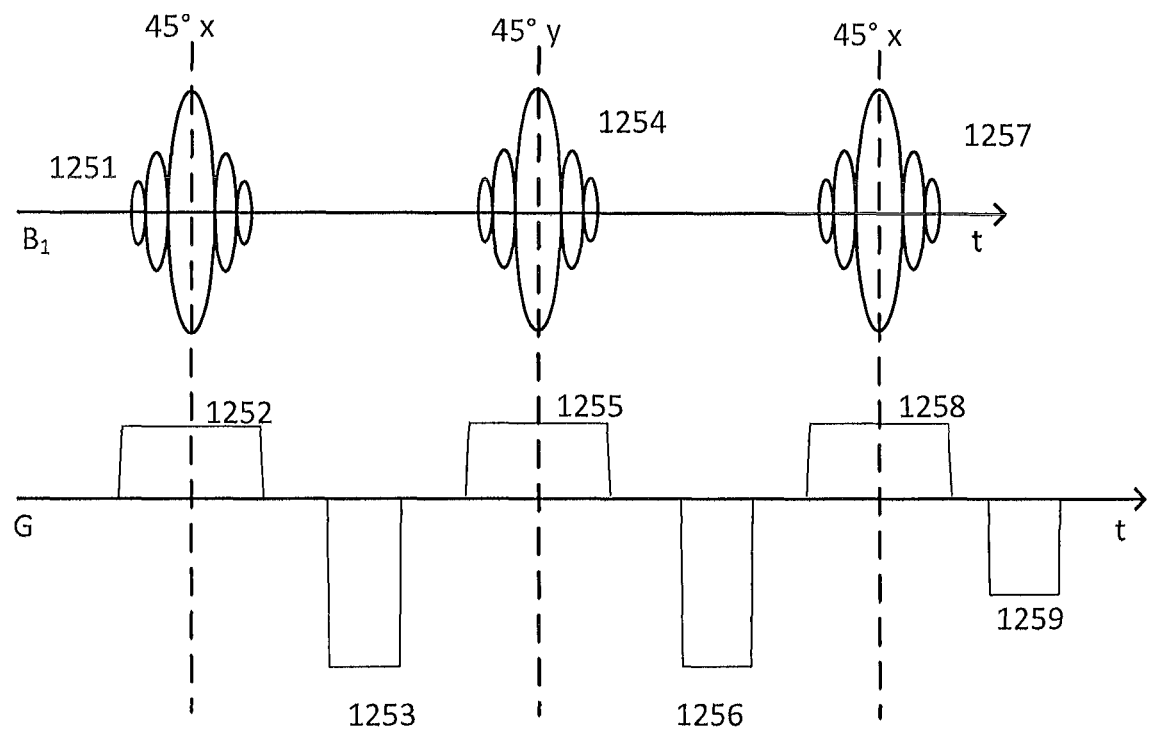
FIG. 17 illustrates another embodiment of an MRI pulse sequence according to an aspect of the present invention that uses three pulses in two axes of rotation to generate a 90 degree excitation pulse

FIG. 17 illustrates a method of performing a rotation equivalent to a 90 degree excitation pulse. In this example this is provided by applying three successive 45 degree rotations. In this example each rotation is applied orthogonally to each previous rotation, and includes application of a final refocusing gradient after all slice selection gradients have been applied. As with previous examples, clockwise rotations of the magnetisations are assumed in the following description, and the initial net magnetisation M lies along the positive z-axis.

As in the previous embodiments, the top plot shows the RF magnetic field pulses B1, which in this example are shaped as sinc pulses. The lower plot illustrates applied magnetic field gradients G. A slice selective rotation generated by the application of a first RF magnetic field pulse 1251 and an associated corresponding magnetic field gradient 1252 are applied. The magnetic field gradient has a magnitude that increases along a direction transverse to a slice being selected. The slice selective rotation caused by first RF magnetic field pulse 1251 is configured to generate a 45 degree rotation (i.e. has a desired rotation of 45 degrees) in the positive direction about the x-axis.

Next a rephasing gradient 1253 is applied with a reversed gradient direction to the first slice selection magnetic field gradient 1252. The re-focussing magnetic field gradient 1253 is generated to re-phase the de-phased magnetisations generated by the first slice selective rotation.

Then a second slice selective rotation is generated by the application of a second RF magnetic field pulse 1254 and an associated corresponding second magnetic field gradient 1255. The magnetic field gradient has a magnitude that increases along a direction transverse to a slice being selected. The slice selective rotation 1254 is configured to generate a 45 degree rotation in the positive direction about the y-axis.

Next a rephasing gradient 1256 is applied with a reversed gradient direction to the second slice selection magnetic field gradient 1255. The re-focussing magnetic field gradient 1256 is generated to re-phase and de-phased magnetisations generated by the first and second slice selective rotation.

Then a third slice selective rotation is generated by the application of a third RF magnetic field pulse 1257 and an associated corresponding third magnetic field gradient 1258. The magnetic field gradient has a magnitude that increases along a direction transverse to a slice being selected. The third slice selective rotation 1257 is also configured to generate a 45 degree rotation in the positive direction about the x-axis. In this example, the third slice selective rotation is generated by application of an RF magnetic pulse and gradient field that are essentially the same as those used the first slice selective rotation. The net result is that the magnetisation M will now lie in the x-y plane.

Lastly a final re-phasing magnetic field gradient 1259 is applied to correct de-phasing of the magnetisation vectors within the ensemble that resulted from the previous slice-selective rotation.

Figure 18:
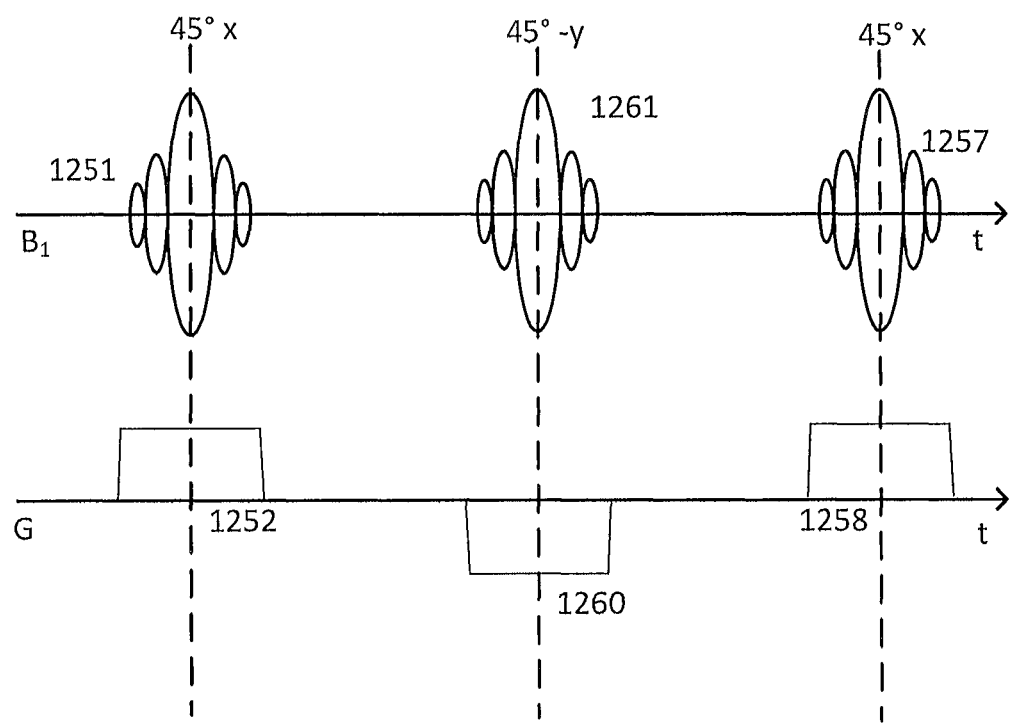
FIG. 18 illustrates an alternative MRI pulse sequence equivalent to that of FIG. 17 to generate a 90 degree excitation pulse.

FIG. 18 illustrates an alternative MRI pulse sequence equivalent to that of FIG. 17, in that it is intended to produce the same effect as a 90 degree excitation pulse, but which uses only a final re-focussing gradient and inverts the direction of the slice selection gradient used for the second slice selective rotation, so that it may also serve to perform some refocussing. As disclosed in connection with the previous embodiment the pulse sequence includes first and third slice selective rotations comprising respective RF magnetic field gradients 1251, 1257, and corresponding slice selection gradients 1252 and 1258. It also includes a final refocussing gradient 1259. However, in a manner analogous to FIG. 10 (and FIG. 15), the pulse sequence of FIG. 18, inverts the direction of the slice selection gradient 1260 used for the second slice selective rotation, so that it may also serve to perform refocussing. Furthermore the second RF magnetic field pulse 1261 is applied with a negative phase when compared to the second RF pulse 1254 of FIG. 17. As previously noted, the multiple slice selective gradients are performed so that their slices are in registration with each other so appropriate frequency offsets will need to be applied to them so that they correctly align along the B0 field.

It is important to note that the present invention should not be considered as being limited to the production of certain specific desired rotations, or using certain specific component rotations or certain specific numbers of fixed rotations. In the examples described herein each individual rotation is less than or equal to the total desired rotation, but the total cumulative rotation performed is greater than the total desired rotation.

Figure 19:
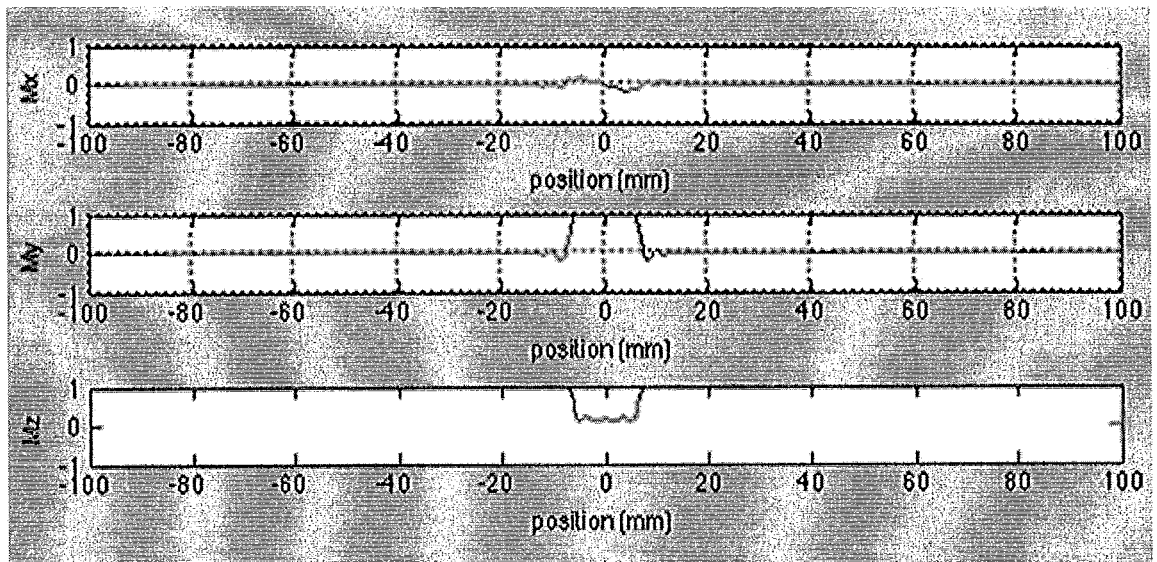
FIGS. 19 and 20 respectively illustrate simulations of the operation of a conventional 90 sinc excitation pulse (FIG. 19) and simulations of the operation of the three component 90 degree excitation pulse of FIG. 17 (FIG. 20).
Figure 20:
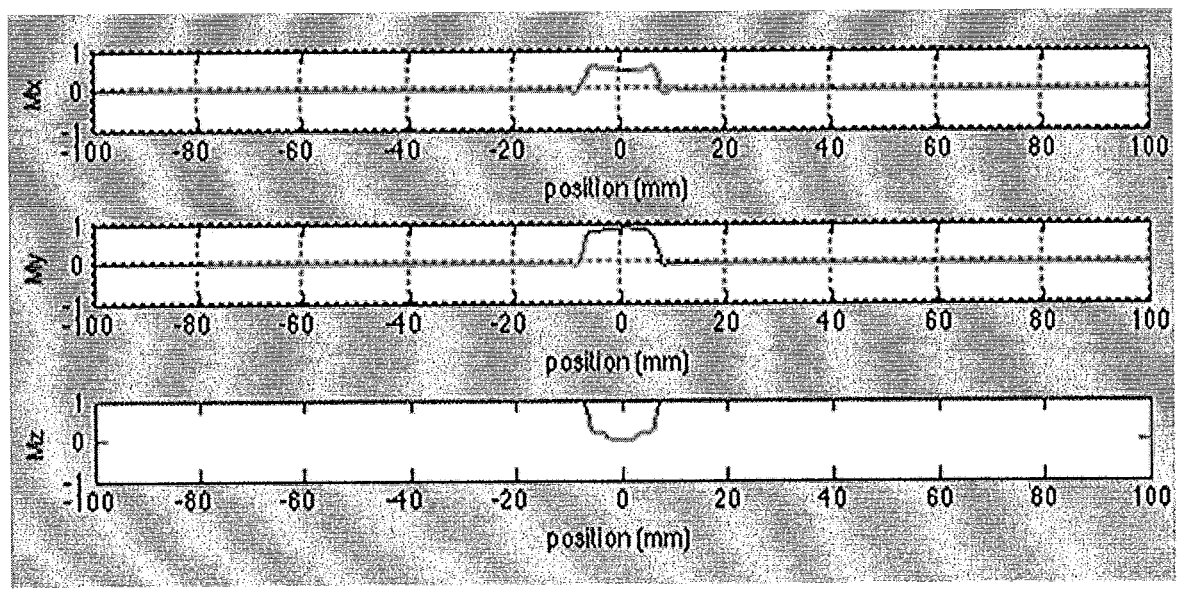

FIGS. 19 and 20 illustrate simulations of the Bloch equations for a conventional 90 degree excitation pulse in (FIG. 19) and that produced by the 90 degree excitation pulse sequence of FIG. 17 (FIG. 20). The conventional 90 degree excitation pulse is ideally intended to move all magnetisation from the z direction and produce zero magnetisation in the x and z direction (i.e. Mx=Mz=0 across the whole slice), and all magnetisation lies in the y direction.

In FIG. 20, simulations for the pulse sequence of FIG. 17 are shown. The pulse aims to have zero magnetisation in the z direction (Mz) and all magnetisation in the x and y plane. As can be seen the response in the x and y directions, produce a relatively flat response across the whole slice. The Mz magnetisation clearly reaches the zero level across the central third of the slice.

Advantageously, the multiple pulse MRI sequences described herein are less sensitive to inhomogeneity in the first RF magnetic field affecting the first rotation angle as the subsequent RF magnetic fields in the MRI sequence can be used to at least partially correct for a deviation of the first rotation angle from the intended angle due to the effect of transverse magnetic field (B1) inhomogeneity. As a result, the effect of the spatial inhomogeneity of the B1 field on the MRI signal is reduced. This is to say that areas of a 2D image of a corresponding 2D slice, in the x-y plane, of a subject that would otherwise be affected by the spatial inhomogeneity, are not affected as much (or not at all if the resultant first rotation angle was 45°, 90° or 135°). Furthermore, in preferred forms the multiple pulse MRI sequences described herein are applied without requiring prior knowledge of which part of the image is affected by inhomogeneity.

Advantageously, imaging of areas that are affected by inhomogeneity are improved without affecting the image obtained from areas that are unaffected by inhomogeneity.

Whilst embodiments of the present invention can be used at any B0 field strength, inhomogeneity in the B1 field may be more prevalent at higher B0 field levels, e.g. at 3 T or above. Hence some embodiments may be advantageously used at B0 field levels of 3 T and above, such as 7 T. However, as discussed below, some embodiments of the present invention also provide improved signal strength (e.g. total received signal energy). Thus whilst B1 inhomogeneity is less of a problem at a B0 level of lower than 3 T, some embodiments may be present advantages. Hence embodiments can be used with B0 filed levels at 1.5 T, above 1.5 T or below 1.5 T.

Figure 21:
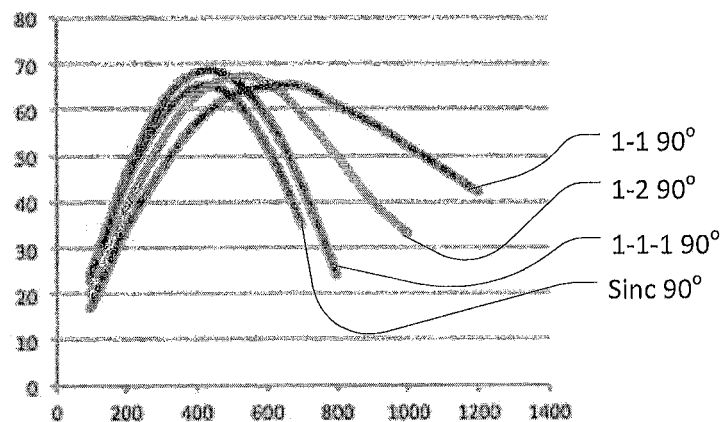
FIG. 21 illustrates simulations of the total received signal strength, for a conventional 90 degree sinc pulse and several exemplary 90 degree pulse sequences of the present invention, plotted over a range of RF signal amplitudes.

FIG. 21 illustrates simulations of the total received signal strength, for a conventional 90 degree sinc pulse (Sinc 90) and the following equivalent 90 degree pulse sequences:

A three component 90 degree pulse, such as that illustrated in FIG. 17 (1-1-1 90);

A two component pulse having pulse components in a rotation angle ratio of 1:2, such as that illustrated in FIG. 4 (1-2 90);

A two component pulse having pulse components in a rotation angle ratio of 1:1(1-1 90).

Each point on each plot corresponds to the total received signal energy from within the selected imaging slice for a given level of input RF amplitude. As will be understood, it is desirable to have higher received signal level and also for the signal level to be relatively consistent across different RF amplitudes.

As can be seen, in each case the multiple-component pulse sequences of embodiments of the present invention achieve a higher peak signal strength than the conventional 90° sinc pulse. Moreover the curves are relatively flatter than the conventional 90° sinc pulse.

Figure 22:
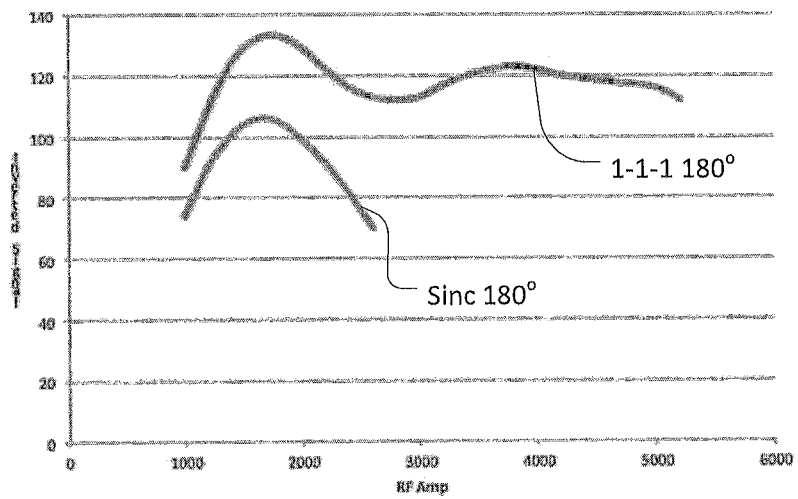
FIG. 22 illustrates simulations of the total received signal strength, for a conventional 180 degree sinc inversion pulse and a three-component 180 degree inversion pulse sequence of the present invention, plotted over a range of RF signal amplitudes.

FIG. 22 illustrates simulations of the total received signal strength from within the selected imaging slice, for a conventional 180 degree sinc pulse (Sinc 180) and a three-component 180 degree inversion pulse sequence of the present invention, as illustrated in FIG. 11, plotted over a range of RF signal amplitudes, (1-1-1 180). As can be seen, the multiple-component pulse sequence of the inventive embodiment achieves a higher peak signal strength than the conventional 180° sinc pulse. Moreover the curve is flatter than the conventional 180° sinc pulse.

Figure 23:
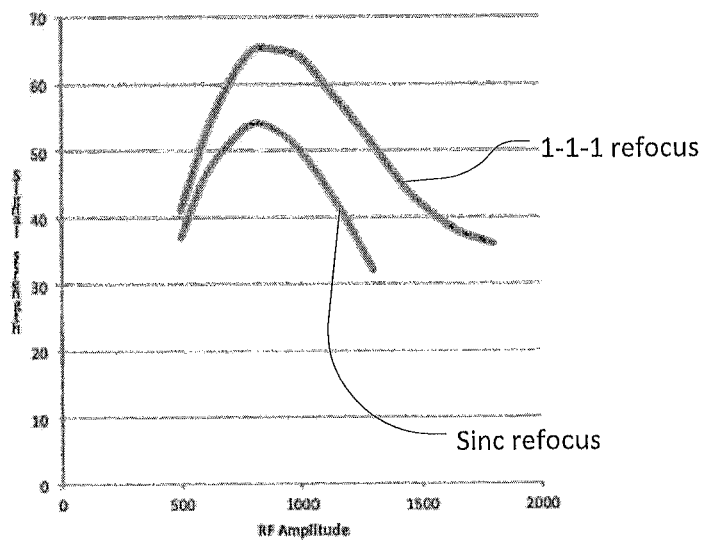
FIG. 23 illustrates simulations of the total received signal strength, for a conventional 180 degree sinc refocussing pulse and a three-component 180 degree refocussing pulse sequence of the present invention, plotted over a range of RF signal amplitudes.

FIG. 23 illustrates simulations of the total received signal strength from within the selected imaging slice, for a conventional 180 degree sinc refocusing pulse (Sinc-refocus) and a three-component 180 degree refocussing pulse sequence of the present invention, as illustrated in FIG. 11, plotted over a range of RF signal amplitudes, (1-1-1 refocus). As can be seen, the multiple-component pulse sequence of the inventive embodiment achieves a higher peak signal strength than the conventional 180° sinc refocusing pulse. Moreover the curve is flatter than the conventional 180° sinc refocussing pulse.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for use in magnetic resonance imaging including:

exposing at least a portion of a subject to a longitudinal magnetic field (B0) such that a net magnetisation vector representing a resultant magnetisation of the nuclear magnetic moments of an ensemble of nuclei in the portion of the subject is longitudinally aligned with the magnetic field (B0);

performing a first slice-selective rotation by:

exposing at least said portion of the subject to a first radio-frequency magnetic field pulse (B1a) and a first magnetic field gradient, said first magnetic field gradient and first radio-frequency magnetic field pulse defining a slice within said portion of the subject and exciting nuclei within the slice, the first radio-frequency magnetic field pulse being configured to rotate the net magnetisation of an ensemble of nuclei within the slice about a first axis by a first angle, such that a first component of the net magnetisation within the slice lies in a first plane including the first axis and a second component of the net magnetisation remains aligned with the magnetic field (B0);

performing a second slice-selective rotation by:

exposing at least said portion of the subject to a second radio-frequency magnetic field pulse (B1b) and a corresponding second magnetic field gradient to excite nuclei within said slice, the second radio-frequency magnetic field pulse being configured to rotate the net magnetisation of the ensemble of nuclei within the slice about a second axis by a second angle, such that at least a portion of the second component of the net magnetisation within said slice that remained aligned with the magnetic field (B0) after the first slice selective rotation, lies in a plane including the second axis of rotation wherein said first axis of rotation is different to said second axis of rotation; and performing a final phase adjustment by:

exposing at least said slice to a final re-phasing magnetic field gradient to correct de-phasing of the magnetisation vectors within the slice that exist after the second slice-selective rotation.

2. The method of claim 1 which further includes performing a third slice-selective rotation by:

exposing at least said portion of the subject to a third radio-frequency magnetic field pulse (B1c) and a corresponding third magnetic field gradient to excite nuclei within said slice, the third radio-frequency magnetic field pulse being configured to rotate the net magnetisation about the first axis by a third angle; and wherein the final phase adjustment is performed after the third slice selective rotation.

3. A method of claim 2 which further includes performing a second phase adjustment before the third slice selective rotation by:

exposing at least said slice to a second re-phasing magnetic field gradient to correct de-phasing of magnetisation vectors within the slice that is a result of the second slice-selective rotation.

4. The method of claim 2, wherein the third angle is substantially the same as the first angle and the second angle.

5. A method of claim 1 which further includes performing a first phase adjustment before the second slice selective rotation by:

exposing at least said portion of the subject to a first re-phasing magnetic field gradient to correct de-phasing of magnetisation vectors within the slice that is a result of the first slice-selective rotation.

6. A method as claimed in claim 5, wherein the first phase adjustment further includes over-correcting said de-phasing of the magnetisation vectors within the slice.

7. A method as claimed in claim 5 wherein the second magnetic field gradient causes re-phasing of the over-corrected magnetisation vectors such that a temporal centre of the second radio-frequency pulse substantially coincides with a time at which the magnetisation vectors within the slice are substantially in phase.

8. A method as claimed in claim 5, wherein any one or more of the following relationships hold between the first magnetic field gradient and the first re-phasing magnetic field gradient:
an integral of the amplitude of first magnetic field gradient over time is equal to an integral of amplitude of the first re-phasing magnetic field gradient over time;
the duration of the first magnetic field gradient is longer than the duration of the first re-phasing magnetic field gradient; and
the magnitude of the first re-phasing magnetic field gradient is at least twice the magnitude of the first magnetic field gradient.

9. A method as claimed in claim 1 wherein, within the portion of the subject, the first magnetic field gradient results in a magnetic field with a magnitude that increases along a first gradient direction, and the second magnetic field gradient results in a magnetic field with a magnitude that decreases along the first gradient direction.

10. A magnetic resonance imaging (MRI) system including:
magnetic field producing means for producing a magnetic field (B0);
magnetic field gradient producing means configured to produce magnetic field gradients to alter the magnetic field B0;
radio-frequency magnetic field generating means configured to produce radio-frequency magnetic fields (B1a and B1b); and
the system being configured to perform a method as claimed in claim 1.

11. The method of claim 1, wherein the second angle is larger than the first angle.

12. A method for use in magnetic resonance imaging including:
exposing at least a portion of the subject to a longitudinal magnetic field (B0) such that a net magnetisation vector representing a resultant magnetisation of the nuclear magnetic moments of an ensemble of nuclei in the portion of the subject, is longitudinally aligned with the magnetic field (B0);
performing a first slice-selective rotation by:
exposing at least said portion of the subject to a first radio-frequency magnetic field pulse (B1a) and a corresponding first magnetic field gradient to excite nuclei within a slice within the portion of the subject, the first radio-frequency magnetic field pulse being configured to rotate the net magnetisation of an ensemble of nuclei within said slice about a first axis by a first angle such that a first component of the net magnetisation in said slice lies in a first plane including the first axis and a second component of the net magnetisation remains aligned with the magnetic field (B0), and wherein within the slice the first magnetic field gradient provides a magnetic field with a magnitude that increases along a gradient direction;
performing a second slice-selective rotation by:
exposing said slice to a second radio-frequency magnetic field pulse (B1b) and corresponding second magnetic field gradient to excite nuclei within the slice, the second radio-frequency magnetic field pulse being configured to rotate the net magnetisation within the slice about a second axis by a second angle such that at least a portion of the second component of the net magnetisation within the slice, that remained aligned with the magnetic field (B0) after the first slice selective rotation, lies in a plane including the second axis of rotation, and wherein the second magnetic field provides a magnetic field with a magnitude that decreases along said gradient direction and at least partly re-phases a de-phasing of the magnetisation vectors within the slice that is a result of the first slice-selective rotation, wherein the first axis of rotation is different to the second axis of rotation.

13. A magnetic resonance imaging (MRI) system including:
magnetic field producing means for producing a magnetic field (B0);
magnetic field gradient producing means configured to produce magnetic field gradients to alter the magnetic field B0;
radio-frequency magnetic field generating means configured to produce radio-frequency magnetic fields (B1a and B1b); and
the system being configured to perform a method as claimed in claim 12.

14. A method for use in magnetic resonance imaging including:
exposing at least a portion of a subject to a longitudinal magnetic field (B0) such that a net magnetisation vector representing a resultant magnetisation of the nuclear magnetic moments of an ensemble of nuclei in the portion of the subject, is longitudinally aligned with the magnetic field (B0);
performing a first slice-selective rotation by:
exposing at least said portion of the subject to a first radio-frequency magnetic field pulse (B1a) and a corresponding first magnetic field gradient to excite nuclei within a slice within the portion subject, the first radio-frequency magnetic field pulse being configured to rotate the net magnetisation within the slice about a first axis by a first angle such that a first component of the net magnetisation within the slice lies in a first plane including the first axis and a second component of the net magnetisation remains aligned with the magnetic field (B0);
performing a second slice-selective rotation by:
exposing the slice to a second radio-frequency magnetic field pulse (B1b) and corresponding second magnetic field gradient to excite nuclei within the slice, the second radio-frequency magnetic field pulse being configured to rotate the net magnetisation within the slice about a second axis by a second angle such that at least a portion of the second component of the net magnetisation within the slice, that remained aligned with the magnetic field (B0) after the first slice selective rotation, lies in a plane including the second axis of rotation; and
performing a third slice-selective rotation by:
exposing at least said portion of the subject to a third radio-frequency magnetic field pulse (B1c) and a corresponding third magnetic field gradient to excite nuclei within the portion of the subject, the third radio-frequency magnetic field pulse being configured to rotate the net magnetisation about the first axis by a third angle.

15. The method of claim 14 which further includes performing a first phase adjustment before the second slice selective rotation by:
exposing at least said portion of the subject to a first re-phasing magnetic field gradient to correct de-phasing of magnetisation vectors within the ensemble of nuclei within the slice that is a result of the first slice-selective rotation.

16. The method of claim 14 which further includes performing a second phase adjustment before the third slice selective rotation by:
exposing at least said portion of the subject to a second re-phasing magnetic field gradient to correct de-phasing of magnetisation vectors within the ensemble of nuclei within the slice that is a result of the second slice-selective rotation.

17. The method of claim 14 wherein the second magnetic field gradient causes re-phasing of the magnetisation vectors within the slice that are de-phased by the first slice selective rotation.

18. A magnetic resonance imaging (MRI) system including:
magnetic field producing means for producing a magnetic field (B0);
magnetic field gradient producing means configured to produce magnetic field gradients to alter the magnetic field B0;
radio-frequency magnetic field generating means configured to produce radio-frequency magnetic fields (B1a and B1b); and
the system being configured to perform a method as claimed in claim 14.

19. The method of claim 14, wherein the first angle, the second angle, and the third angle are equal.

\* \* \* \* \*